United States Patent
Hawiger et al.

(10) Patent No.: US 8,420,096 B2
(45) Date of Patent: Apr. 16, 2013

(54) CELL-PENETRATING SOCS POLYPEPTIDES THAT INHIBIT CYTOKINE-INDUCED SIGNALING

(75) Inventors: Jack J. Hawiger, Nashville, TN (US); Daewoong Jo, Gwangju (KR)

(73) Assignee: Vanderbilt University, Nashville, TN (US)

( * ) Notice: Subject to any disclaimer, the term of this patent is extended or adjusted under 35 U.S.C. 154(b) by 214 days.

(21) Appl. No.: 10/589,726

(22) PCT Filed: Mar. 4, 2005

(86) PCT No.: PCT/US2005/007523
§ 371 (c)(1),
(2), (4) Date: Nov. 6, 2008

(87) PCT Pub. No.: WO2005/086800
PCT Pub. Date: Sep. 22, 2005

(65) Prior Publication Data
US 2009/0209458 A1   Aug. 20, 2009

Related U.S. Application Data

(60) Provisional application No. 60/550,037, filed on Mar. 4, 2004.

(51) Int. Cl.
*A61K 38/00* (2006.01)
*A61K 38/16* (2006.01)
*A61K 38/17* (2006.01)
*A61P 31/04* (2006.01)
*A61P 29/00* (2006.01)

(52) U.S. Cl.
USPC ............... 424/184.1; 424/185.1; 424/192.1; 514/2.3; 514/2.4; 514/2.7; 514/12.2; 530/350

(58) Field of Classification Search .................. None
See application file for complete search history.

(56) References Cited

U.S. PATENT DOCUMENTS

| | | | |
|---|---|---|---|
| 3,610,795 A | 10/1971 | Antoine | |
| 6,323,317 B1 | 11/2001 | Hilton et al. | |
| 6,905,842 B1 | 6/2005 | Hilton et al. | |
| 7,049,418 B2 | 5/2006 | Hilton et al. | |
| 2011/0229525 A1 * | 9/2011 | Hawiger et al. | 424/278.1 |

FOREIGN PATENT DOCUMENTS

| | | |
|---|---|---|
| EP | 0045665 | 9/1985 |
| WO | 98/20023 A1 | 5/1998 |
| WO | WO 99/03993 | 1/1999 |
| WO | 99/23220 A1 | 5/1999 |
| WO | WO-99/49879 A1 * | 10/1999 |
| WO | 0129178 A2 | 4/2001 |

OTHER PUBLICATIONS

Kaufman et al. Blood 94: 3178-3184, 1999.*
Wang et al. Rapid analysis of gene expression (RAGE) facilitates universal expression profiling. Nucleic Acids Res 27(23): 4609-4618, 1999.*
Wigley et al. Site-specific transgene insertion: an approach. Reprod Fertil Dev 6: 585, 588, 1994.*
Phillips, A., The challenge of gene therapy and DNA delivery. J Pharm Pharmacology 53: 1169-1174, 2001.*
Hanada et al. Negative regulation of cytokine signaling by CIS/SOCS family proteins and their roles in inflammatory diseases. Rev Physiol Biochem Pharmacol 149: 72-86, 2003.*
Abrahmsen L et al., "Engineering subtilisin and its subtrates for efficient ligation of peptide bonds in aqueous solutions," Biochemistry, 30:4151-4159 1991.
Alexander and Douglas J. Hilton. "The role of suppressors cytokine signaling (SOCS)" 22:503-29, 2004.
Alexander et al. "Suppressors of Cytokine signaling Immune system," Nat Rev (SOCS) 2:1-7, 2002.
Alexander, W.S., "Suppressors of cytokine signalling (SOCS) in the immune system" Nat Rev Immunol 2, 410-6, 2002.
Almquist et al., "Synthesis and biological activity of a ketomethylene," J. Med. Chem 23:1392-1398 (1980).
Arad, G., Levy, R., Hillman, D. & Kaempfer, R. "Superantigen antagonist protects against lethal shock and defines a new domain for T-cell activation." Nat Med 6, 414-21 (2000).
Baggiolini M et al. "Interleukin-8, a chemotactic and inflammatory cytokine," FEBS Lett. 307:97-101, 1992.
Bagshawe, et al., "A cytotoxic agent can be generated selectively at cancer sites." Br. J. Cancer, 58:700-703, (1988).
Bagshawe, K.D., "The First Bagshawe lecture. Towards generating cytotoxic agents at cancer sites." Br. J. Cancer, 60:275-281, (1989).
Balaban, N. & Rasooly, A. "Analytical chromatography for recovery of small amounts of Staphylococcal enterotoxins from food." Int J Food Microbiol 64, 33-40 (2001).
Battelli, et al., "T lymphocyte killing by a xanthine-oxidase-containing immunotoxin." Cancer Immunol. Immunother., 35:421-425, (1992).
Benner, "Expanding the genetic lexicon: incorporating non-standard amino acids into proteins by ribosome-based synthesis." TIB Tech, 12:158-163 (1994).
Bjorbaek, C.et al. "The role of SOCS-3 in leptin signaling and leptin resistance." J. Biol. Chem.274, 30059-30065, 1999.
Brown and Greene, "Molecular and cellular mechanisms of receptor-mediated endocytosis." DNA and Cell Biology 10:6, 399-409 (1991).
Cahill et al., "Site-specific mutagenesis with unnatural amino acids." TIBS, 14(10):400-403 (1989).
Car, B.D. et al. "Interferon gamma receptor deficient mice are resistant to endotoxic shock." J Exp Med 179, 1437-44 (1994).
Cavaillon, J.M., Adib-Conquy, M., Fitting, C., Adrie, C. & Payen, D. "Cytokine cascade in sepsis." Scand J Infect Dis 35, 535-44 (2003).
Clark Lewis I et al., "Chemical synthesis, purification, and characterization of two inflammatory proteins, Neutrophil activating peptide 1 (interleukin-8) and neutrophil activating peptid 2." Biochemistry, 30:3128 (1991).
Clark Lewis I et al., "Structural requirements for interleukin-8 function identified by design of analogs and CXC chemokine hybrids." J.Biol.Chem., 269:16075-16081 (1994).

(Continued)

Primary Examiner — Bridget E Bunner
(74) *Attorney, Agent, or Firm* — Novak Druce Connolly Bove + Quigg LLP; Amy A. Dobbelaere

(57) ABSTRACT

Disclosed are compositions and methods related to cell-penetrating suppressor of cytokine signaling (SOCS) proteins that inhibit cytokine-induced signaling.

21 Claims, 7 Drawing Sheets

OTHER PUBLICATIONS

Clark, N.M., Hershberger, E., Zervosc, M.J. & Lynch, J.P., 3rd. "Antimicrobial resistance among gram-positive organisms in the intensive care unit." Curr Opin Crit Care 9, 403-12 (2003).

Croker, B.A. et al. "SOCS3 negatively regulates IL-6 signaling in vivo." Nat Immunol 4, 540-5 (2003).

Dawson et al. Synthesis of Proteins by Native Chemical Ligation. Science, 266:776 779, 1994.

De Lisle Milton, R.C. et al., "Synthesis of Proteins by Chemical Ligation of Unprotected Peptide Segments: Mirror-Image Enxyme Molecules, D- & L-HIV Protease Analogs" Techniques in Protein Chemistry IV. Academic Press, New York, pp. 257 267 (1992).

Dinges, M.M., Orwin, P.M. & Schlievert, P.M. "Exotoxins of *Staphylococcus aureus*." Clin Microbiol Rev 13, 16-34, (2000).

Drakas R et al. "A modified tandem affinity purification tag technique for the purification of protein complexes in mammalian cells." Proteomics 5:132-137 (2005).

Emanuelli, B. et al, "SOCS-3 Is an insulin-induced negative regulator of insulin signaling." J.Biol. Chem. 275, 15985-15991 (2000).

Fey, P.D. et al. "Comparative molecular analysis of community- or hospital-acquired methicillin-resistant *Staphylococcus aureus*." Antimicrob Agents Chemother 47, 196-203 (2003).

Fitzgerald, K.A. et al. "LPS-TLR4 signaling to IRF-3/7 and NF-kappaB involves the toll adapters TRAM and TRIF." J Exp Med 198, 1043-55 (2003).

Hann M. et al. "On the double bond isostere of the peptide bond: preparation of an enkephalin analogue." Chem. Soc Perkin, 307-314 (1982).

Hawiger, J. "Cellular import of functional peptides to block intracellular signaling." Curr Opin Immunol 9, 189-94 (1997).

Hawiger, J. "Innate immunity and inflammation: a transcriptional paradigm." Immunol Res 23, 99-109 (2001).

Hawiger, J. "Noninvasive intracellular delivery of functional peptides and proteins." Curr Opin Chem Biol 3, 89-94 (1999).

Hoebe, K. et al. "Identification of Lps2 as a key transducer of MyD88-independent TIR signaling." Nature 424, 743-8 (2003).

Holladay et al. "Synthesis of hydroxyethlyene and ketomethylene dipeptide isosteres, Tetrahedron." Lett 24:4401-4404 (1983).

Hotamisligil, G. S., "Inflammatory pathways and insulin action.", G.S. Int. J. Obes 27, S53-55,(2003).

Hruby, "Conformational restrictions of biologically active peptides via amino acid chain groups." Life Sci 31:189-199 (1982).

Hudson, D. et al., "Methionine enkephalin and isosteric analogues. I. Synthesis on a phenolic resin support." Int J Pept Prot Res 14:177-185 (1979).

Hughes et al.,"Monoclonal antibody targeting of lipsomes to mouse lung in vivo." Cancer Research, 49:6214-6220, (1989).

Ibba and Hennecke, "Towards engineering proteins by site-directed incorporated in vivo of non-natural amino acids." Bio/technology, 12:678-682 (1994).

Ibba,M., "Strategies for in vitro and in vivo translation with non-natural amino acids." Biotechnology & Genetic Engineering Reviews 13:197-216 (1995).

Itakura et al., "Synthesis and use of synthetic oligonucleotides." Rev. Biochem. 53:323-356 (1984.

Inagaki-Ohara K, Hanada T, Yoshimura A., "Negative regulation of cytokine signaling and inflammatory diseases." Curr Opin Pharmacol. 3 :435-42 2003.

Ivashkiv LB, Tassiulas I., "Can SOCS make arthritis better?" J Clin Invest.; 111, 795-7 2003.

Jaeger et al., "Predicting optimal and suboptimal secondary structure for RNA." Methods Enzymol. 183:281-306, 1989.

Jaeger et al., "Improved predictions of secondary structures for RNA." Proc. Natl. Acad. Sci. USA 86:7706-7710, 1989.

Jennings-White et al., "Synthesis of ketomethylene analogs of dipeptides." Tetrahedron Lett 23:2533-2534 (1982).

Jo et al., "Intracellular Protein Therapy with SOCS3 Inhibits Inflammation and Apoptosis." Nature Med., 11, 892-898 2005.

Jo, D. et al., "Cell cycle-dependent transduction of cell-penetrating Cre recombinase proteins." J Cell Biochem 89, 674-87 (2003).

Jo, D. et al., "Epigenetic regulation of gene structure and function with a cell-permeable Cre recombinase." Nat Biotechnol 19, 929-33 (2001).

Krebs, D.L. & Hilton, D.J. "SOCS proteins: negative regulators of cytokine signaling." Stem Cells 19, 378-87 (2001).

Krebs, D.L. & Hilton, D.J. "SOCS: physiological suppressors of cytokine signaling." J Cell Sci 113, 2813-9 (2000).

Kunkel et al. "Rapid and efficient site-specific mutagenesis without phenotypic selection." Methods Enzymol. 1987:154:367, 1987.

Lang, R. et al., "SOCS3 regulates the plasticity of gp130 signaling." Nat Immunol 4, 546-50 (2003).

Larsen et al., "Suppressors of Cytokine Signaling: SOCS." APMIS Dec. 2002, vol. 110. No. 12, pp. 833-844.

Lee, J.Y. & Sullivan, K.E., "Gamma interferon and lipopolysaccharide interact at the level of transcription to induce tumor necrosis factor alpha expression." Infect Immun 69, 2847-52 (2001).

Letsinger et al., "Cholesteryl-conjugated oligonucleotides: Synthesis properties and activity as inhibitors of replication of human immunodeficiency virus cell culture." Proc. Natl. Acad. Sci. USA, 86, 6553 6556, 1989.

Litzinger and Huang, Biochimica et Biophysica Acta, 1104:179-187, (1992).

Liu, D. et al. "Suppression of Staphylococcal enterotoxin B-induced Toxicity by a Nuclear Import Inhibitor." J Biol Chem 279, 19239-46 (2004).

Madsen, J.M. "Toxins as weapons of mass destruction. A comparison and contrast with biological-warfare and chemical-warfare agents." Clin Lab Med 21, 593-605 (2001).

Mattix, M.E., Hunt, R.E., Wilhelmsen, C.L., Johnson, A.J. & Baze, W.B. "Aerosolized Staphylococcal enterotoxin B-induced pulmonary lesions in rhesus monkeys (*Macaca mulatta*)." Toxicol Pathol 23, 262-8 (1995).

Miethke, T. et al. "T cell-mediated lethal shock triggered in mice by the superantigen Staphylococcal enterotoxin B: critical role of tumor necrosis factor." J Exp Med 175, 91-98 (1992).

Morley, "Modulation of the Action of regulatory peptides by structural modification." Trends Pharm Sci pp. 463-468,1980.

Narang et al., "Chemical synthesis of Dexoxyoligonucleotides by the modified trimester method." Methods Enzymol., 65:610-620 (1980).

Needleman and Wunsch, "A general method applicable to the search for similarities in the amino acid sequence of two proteins." J. Mol Biol. 48: 443-453 (1970).

Nielsen et al., "Petide nucleic acid (PNA). A DNA mimic with a peptide backbone." Bioconjug. Chem. 5:3-7 (1994).

NIH Grant No. HL68744. "Functional Genomics of Inflammation", Jan. 26, 2001.

NIH Grant No. HL69542. "Superantigen-Induced Vascular Injury and DIC", Mar. 27, 2001.

O'Keefe, G.M., Nguyen, V.T., Ping Tang, L.L. & Benveniste, E.N. "IFN-gamma regulation of class II transactivator promoter IV in macrophages and microglia: involvement of the suppressors of cytokine signaling-1 protein." J Immunol 166, 2260-9 (2001).

Oshiumi, H. et al. "TIR-containing adapter molecule (TICAM)-2, a bridging adapter recruiting to toll-like receptor 4 TICAM-1 that induces interferon-beta." J Biol Chem 278, 49751-62 (2003).

Pearson and Lipman, "Improved tools for biological sequence comparison." Proc. Natl. Acad. Sci. U.S.A. 85: 2444-2448 (1988).

Pfeffer, K. et al., "Mice deficient for the 55 kd tumor necrosis factor receptor are resistant to endotoxic shock, yet succumb to L. monocytogenes infection." Cell 73, 457-67 (1993).

Pietersz and McKenzie, "Antibody conjugates for the treatment of cancer." Immunolog. Reviews, 129:57-80, (1992).

Poltorak, A. et al. "Defective LPS signaling in C3H/HeJ and C57BL/10ScCr mice: mutations in TIr4 gene." Science 282, 2085-8 (1998).

Prescilla et al. http://www.emedicine.com, Immunology of Transplant Rejection, updated Jun. 20, 2003).

Rajagopalan, G., Smart, M.K., Krco, C.J. & David, C.S. "Expression and function of transgenic HLA-DQ molecules and lymphocyte development in mice lacking invariant chain." J Immunol 169, 1774-83 (2002).

Rizo and Gierasch, "Constrained peptides: models of bioactive peptides and protein substructures." Ann. Rev. Biochem. 61:387-418 (1992).

Roffler, et al., "Anti-neoplastic glucuronide prodrug treatment of human tumor cells targeted with a monoclonal-enzyme conjugate." Biochem. Pharmacol, 42:2062-2065, (1991).

Rottapel R., "Putting the brakes on arthritis: can suppressors of cytokine signaling (SOCS) suppress rheumatoid arthritis?" J Clin Invest. 108 :1745-7(2001).

Rui, L., Yuan, M., Frantz, D., Shoelson, S. & White, M.F. "SOCS-1 and SOCS-3 block insulin signaling by ubiquitin-mediated degradation of IRS1 and IRS2." J Biol Chem 277, 42394-8 (2002).

Sambrook et al., Molecular Cloning: A Laboratory Manual, 2nd Edition (Cold Spring Harbor Laboratory Press, Cold Spring Harbor, N.Y., 1989) Chapter 5 "Enzymes Used in Molecular Cloning".

Sambrook et al., Molecular Cloning: A Laboratory Manual, 2nd Edition (Cold Spring Harbor Laboratory Press, Cold Spring Harbor, N.Y., 1989) Chapter 6 "Gel Electrophoresis of DNA".

Schnolzer, M et al., "Constructing proteins by dovetailing unprotected synthetic peptides: Backbone-engineered HIV protease." Science, 256:221-5 (1992).

Senter, et al., "Generation of 5-flourouracil from 5-fluorocytosine by monoclonal antibody-cytosine deaminase conjugates." Bioconjugate Chem., 2:447-451, (1991).

Senter, et al., "Generation of cytotoxic agents by targeted enzymes." Bioconjugate Chem., 4:3-9, (1993).

Shouda, T. et al., "Induction of the cytokine signal regulator SOCS3/CIS3 as a therapeutic strategy for treating inflammatory arthritis." J Clin Invest 108, 1781-8 (2001).

Smith and Waterman, Comparison of biosequences, Adv. Appl. Math. 2: 482-489 (1981).

Spatola et al., "Structure-activity relationships of enkephalins containing serially replaced thimethylene amide bond surrogates." Life Sci 38:1243-1249 (1986).

Spatola, A. F., Vega Data (Mar. 1983), vol. 1, Issue 3, Peptide Backbone Modifications: A Structure-Activity Analysis of Peptides Containing Amide Bond Surrogates. (general review), Chap 5., pp. 267-357.

Starr R, Hilton DJ SOCS: suppressors of cytokine signaling. Int J Biochem Cell Biol.30(10):1081-5 (Oct. 1998).

Starr, R. et al. "A family of cytokine-inducible inhibitors of signaling." Nature 387, 917-21 (1997).

Stoiber, D. et al. "Lipopolysaccharide induces in macrophages the synthesis of the suppressor of cytokine signaling 3 and suppresses signal transduction in response to the activating factor IFN-gamma." J Immunol 163, 2640-7 (1999).

Suzuki, A. et al. "CIS3/SOCS3/SSI3 plays a negative regulatory role in STAT3 activation and intestinal inflammation." J Exp Med 193, 471-81 (2001).

Thorson et al., "A Biosynthetic Approach for the Incorporation of Unnatural Amino Acids Into Proteins" Methods in Molecular Biology, vol. 77: 43-73 (1991).

Uysal, K.T. et al, "Protection from obesity-induced insulin resistance in mice lacking TNF function." Nature 389:610-614 1997.

Veach, R.A. et al. "Receptor/transporter-independent targeting of functional peptides across the plasma membrane." J Biol Chem 279, 11425-31 (2004).

Yasuda, S., Nagaki, M. & Moriwaki, H., "*Staphylococcal enterotoxin* B induces hepatic injury and lethal shock in endotoxin-resistant C3H/HeJ mice despite a deficient macrophage response." J Endotoxin Res 8, 253-61 (2002).

Yasukawa, H. et al. "IL-6 induces an anti-inflammatory response in the absence of SOCS3 in macrophages." Nat Immunol 4, 551-6 (2003).

Yasukawa, H., Sasaki, A. & Yoshimura, A. "Negative regulation of cytokine signaling pathways." Annu Rev Immunol 18, 143-64 (2000).

Yeung, R.S. et al. "Human CD4 and human major histocompatibility complex class II (DQ6) transgenic mice: supersensitivity to superantigen-induced septic shock." Eur J Immunol 26, 1074-82 (1996).

Zhang, J.G. et al. "The SOCS box of suppressor of cytokine signaling-1 is important for inhibition of cytokine action in vivo." Proc Natl Acad Sci U S A, 98, 13261-5 (2001).

Zoller, "New recombinant DNA methodology for protein engineering." Current Opinion in Biotechnology, 3:348-354 (1992).

Zuker, "On finding all suboptimal foldings of an RNA molecule." M. Science 244:48-52, 1989.

Farrell, et al., "Signalling links in the liver: Knitting SOCS with fat and inflammation" Journal of Hepatology, Munksaard International Publishers, Copenhagen, DK, vol. 43, No. 1, Jul. 1, 2005, pp. 193-196.

* cited by examiner

CELL-PENETRATING SOCS POLYPEPTIDES THAT INHIBIT CYTOKINE-INDUCED SIGNALING

CROSS-REFERENCE TO RELATED APPLICATION

This application claims priority to U.S. provisional application Ser. No.: 60/550,037 filed Mar. 4, 2004, which is incorporated herein by reference in its entirety.

STATEMENT OF FEDERALLY SPONSORED RESEARCH

This invention was made with partial government support under NIH Grant Nos. HL69542 HL68744, and HL-62356. The United States government has certain rights in the invention.

SEQUENCE LISTING

The instant application contains a Sequence Listing which has been submitted in ASCII format via EFS-Web and is hereby incorporated by reference in its entirety. Said ASCII copy, created on Feb. 21, 2012, is named 20004200.txt and is 53,194 bytes in size.

BACKGROUND

Cytokines and chemokines are proteins made by cells that affect the behavior of other cells. Cytokines made by leukocytes and lymphocytes are often called interleukins (IL) or lymphokines. Cytokines act on specific cytokine receptors on the cells they affect. Binding to the cognate receptor induces activity in the cell such as growth, differentiation, migration or death. Several cytokines and chemokinesplay key roles in mediating acute inflammatory reactions, namely IL-1 beta, TNF-alpha, IL-6, IL-11, IL-12, interferon gamma, IL-8 and other chemokines. Receptors for hemopoietic growth factors, GCSF, and GM-CSF share structural similarity with cytokine receptors and influence the production and function of leukocytes in inflammation.

The production of pro-inflammatory cytokines and chemokines by cells of the innate immune system play an important role in mediating the initial host defense against invading pathogens. Furthermore, the inability to regulate the nature or duration of the host's inflammatory response can often mediate detrimental host effects as observed in acute and chronic inflammatory diseases. For example, in the early stages of sepsis, the host's inflammatory response is believed to be in a hyperactive state with a predominant increase in the production of pro-inflammatory cytolcines that mediate host tissue injury and lethal shock. Thus, the ability of the innate immune system to dictate the levels of pro- and anti-inflammatory cytokine production is critical in limiting or modulating the nature of the host inflammatory response. This ability is conferred by a family of physiologic intracellular proteins termed suppressors of cytokine signaling (SOCSs).

There is a need in the art for methods and compositions capable of inhibiting cytokine-induced signaling, thereby controlling inflammation and associated disorders.

SUMMARY

Disclosed are methods and compositions related to cell-penetrating suppressor of cytokine signaling (SOCS) proteins.

BRIEF DESCRIPTION OF THE DRAWINGS

The accompanying drawings, which are incorporated in and constitute a part of this specification, illustrate several embodiments and together with the description illustrate the disclosed compositions and methods.

FIG. 1A shows the structure of mouse SOCS3 protein. FIG. 1B shows the design of recombinant SOCS3 proteins that contained membrane-translocating motif (AAVLLPVLLAAP, SEQ ID NO:2), histidine tag for affinity purification (MGSSHHHHHHSSLVPRGSH, SEQ ID NO:1), and cargo (SOCS3). FIG. 1C shows expression of SOCS3 fusion proteins in E. coli before (−) and after (+) induction with IPTG monitored by SDS-PAGE and stained with Coomassie blue. The name of each protein (His-SOCS3 (SEQ ID NO:7), HS3 (SEQ ID NO:22); His-SOCS3-MTM, (SEQ ID NO:8) HS3M (SEQ ID NO:19); His-MTM-SOCS3 (SEQ ID NO:9), and HMS3 (SEQ ID NO:21)), the size (number of amino acids), yield purified in soluble form from E. coli cultures (mg/L) and recovery (%) in soluble form from denatured form are indicated.

FIG. 2A shows fluorescence confocal laser scanning microscopy shows intracellular localization of recombinant SOCS3 proteins. RAW cells were incubated with 1 μM FITC-labeled proteins (FITC-HS3, FITC-HS3M & FITC-HMS3) or an equimolar concentration of unconjugated FITC (FITC only). Cell surface-absorbed proteins were degraded by the treatment of unfixed RAW cells with proteinase K. The 0.5-micrometer midcell section demonstrates an apparent intracellular localization of CP-SOCS3 (FIG. 2A, top). A Nomarski image of the same cells shows (FIG. 2A, bottom). FIG. 2B shows the levels of phosphorylated STAT1 untreated (gray color) and treated with IFN-γ were compared to the levels in IFN-γ-treated RAW cells that were pulsed with 10 μM of HS3, HS3M or HMS3. FIG. 2C shows concentration-dependent inhibition of STAT1 phosphorylation. Cells were pretreated with different concentration (3, 6 & 12 μM) of SOCS3 proteins (HS3, HS3M & HMS3) for 1 h followed by treatment with agonists (100 ng/ml LPS+10 U/ml IFN-γ) for 15 min. FIG. 2D shows immunoblotting analysis confirms the inhibition of phosphorylation of STAT1 by CP-SOCS3. Cells were pretreated with different concentration (3 & 6 μM) of SOCS3 proteins (HS3, HS3M & HMS3) for 1 h followed by exposing to agonists (100 ng/ml LPS+30 U/ml IFN-γ) for 15 min. Denatured whole cell lysates were prepared and analyzed by the Western method, using antibody against phospho (pY701)-specific STAT1. FIG. 2E shows inhibition of MCP-1 (black stripped), TNF-α (red), and IL-6 (blue) expression by CP-SOCS3 in cultured AMJ2-C8 macrophages. FIG. 2F shows inhibition of TNF-α (red) and IL-6 (blue) expression by CP-SOCS3 in primary macrophages isolated from peritoneal exudates of C3H/Hej mice. Error bars in c and e-f indicate the +/−S.D. of the mean value derived from each assay done in triplicate.

FIG. 3A shows FACS analysis of leukocytes and lymphocytes isolated from whole blood (blood leukocytes/lymphocytes) and spleen cells (splenocytes) of C3H/HeJ mice 1 h after intraperitoneal injection of diluent, unconjugated free FITC (1 μM, FITC-only;) and FITC-conjugated SOCS3 proteins (1 μM, FITC-HS3; FITC-HS3M; & FITC-HMS3). FIG. 3B shows persistence of FITC-conjugated CP-SOCS3 in cells prepared from C3H/HeJ mice at different time points after intraperitoneal injection of FITC-conjugated CP-SOCS3 protein (1 μM, FITC-HMS3, 2 h; light blue, 8 h; blue & 24 h; green) and unconjugated free FITC (FITC-only, 2 h; red, 8 h; dark yellow, 8 h; magenda). FACS analysis was performed immediately after cell preparation without fixation and following treatment with proteinase K to degrade cell-surface-bound SOCS3 proteins.

FIG. 4A shows IL-6 measured by a cytometric bead array (CBA) in blood plasma from saphenous vein of C3H/HeJ mice at indicated intervals (0.5, 1.5, 4 and 6 h) after SEB/D-galactosamine challenge. Error bars indicate the +/−S.D. of the mean value derived from each assay done in 8 or 9 mice. FIG. 4B shows total splenocytes were obtained from the spleen isolated from the C3H/HeJ mice that survived 48 h following ip administration of SEB and D-galactosamine. Cell surface-expressed MHC class II molecules on CD11b-positive cells from mice that were not challenged (untreated) or challenged with agonists (SEB/D-galactosamine) only (agonists), plus treated with SOCS3 proteins (HS3, HS3M or HMS3) were measured. FIG. 4C shows survival of mice treated with diluent, HS3, HS3M or HMS3 is shown. P values shown represent the significance of the difference between the diluent-treated and SOCS3 proteins-treated mice. Each group comprised of 10 or 12 mice.

FIG. 6A shows the structure and design of cell-penetrating SOCS-3. FIG. 6B shows the structure of SOCS-3 containing MTM. FIG. 6C shows the structure of SOCS-1 from a mouse, including the three domains SH2, KIR, and SOCS-box. Also shown are full length forms as well as truncated forms.

DETAILED DESCRIPTION

Figure 1:
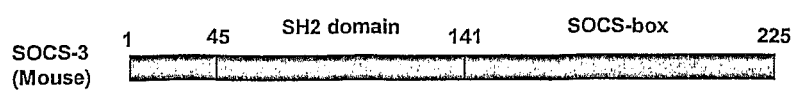
FIGS. 1A-1C show the structure, design, expression and purification of recombinant cell penetrating SOCS3 proteins.
Figure 1:
Figure 1:
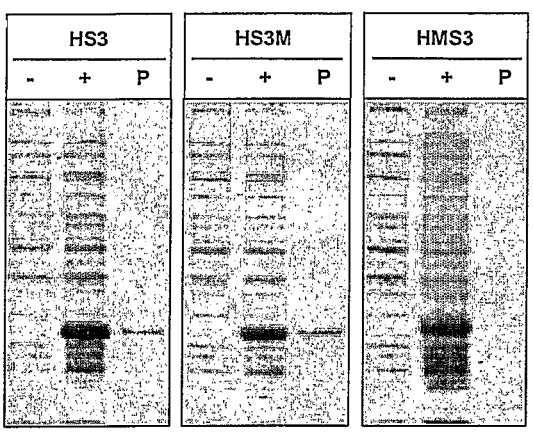

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and ranges between values are also disclosed, as appropriately understood by the skilled artisan. For example, if the value "10" is disclosed the "less than or equal to 10"as well as" greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

The terms "higher," "increases," "elevates," or "elevation" refer to increases above basal levels, or as compared to a control. The terms "low," "lower," "inhibits," "inhibition," "reduces," or "reduction" refer to decreases below basal levels, or as compared to a control. For example, basal levels are normal in vivo levels prior to, or in the absence of, inflammation or the addition of an agent which causes inflammation.

The term "mediate" or "mediation" and "modulate" or "modulation" means to regulate, or control, in particular to increase, enhance, elevate, or alternatively to lower, inhibit, suppress, or reduce. The terms "mediate" and "modulate" are used interchangeably throughout.

"Inflammation" or "inflammatory" is defined as the reaction of living tissues to injury, infection, or irritation. Anything that stimulates an inflammatory response is said to be inflammatory.

"Inflammatory disease" is defined as any disease state associated with inflammation. Examples of inflammatory disease include, but are not limited to, pneumonia and pneumonitis, asthma, atopic dermatitis, contact dermatitis, meningitis and encephalitis, glomerulonephritis, hepatitis, systemic lupus erythematosus, rheumatoid arthritis, reactive arthritis, spondyloarthritis, systemic vasculitis, insulin dependent diabetes mellitus, multiple sclerosis, experimental allergic encephalomyelitis, Sjögren's syndrome, graft versus host disease, inflammatory bowel disease including Crohn's disease, ulcerative colitis, and scleroderna. Inflammatory diseases also includes autoimmune diseases such as myasthenia gravis, Guillain-Barré disease, primary biliary cirrhosis, hepatitis, hemolytic anemia, uveitis, Grave's disease, pernicious anemia, thrombocytopenia, Hashimoto's thyroiditis, oophoritis, orchitis, adrenal gland diseases, anti-phospholipid syndrome, Wegener's granulomatosis, Behcet's disease, polymyositis, dermatomyositis, vitiligo, ankylosing spondylitis, Pemphigus vulgaris, psoriasis, dermatitis herpetiformis, Addison's disease, Goodpasture's syndrome, Basedow's disease, thrombocytopenic purpura, allergy; and cardiomyopathy.

"Infection" or "infectious process" is defined as one organism being invaded by any type of foreign material or another organism. The results of an infection can include growth of the foreign organism, the production of toxins, and damage to the host organism. Infection includes prion, viral, bacterial, parasitic, and fungal infections, for example.

"Liver toxicity" is defined as an abnormal accumulation of toxic substances in the liver. A number of criteria can be used to assess the clinical significance of toxicity data: (a) type/severity of injury, (b) reversibility, (c) mechanism of toxicity, (d) interspecies differences, (e) availability of sensitive biomarkers of toxicity, (e) safety margin (non toxic dose/pharmacologically active dose), and (f) therapeutic potential.

"Cancer therapy" is defined as any treatment or therapy useful in preventing, treating, or ameliorating the symptoms associated with cancer. Cancer therapy can include, but is not limited to, apoptosis induction, radiation therapy, and chemotherapy.

"Transplant" is defined as the transplantation of an organ or body part from one organism to another.

"Transplant rejection" is defined as an immune response triggered by the presence of foreign blood or tissue in the body of a subject. In one example of transplant rejection, antibodies are formed against foreign antigens on the transplanted material.

As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. Preferably, the subject is a mammal such as a primate, and, more preferably, a human.

The terms "control levels" or "control cells" are defined as the standard by which a change is measured, for example, the controls are not subjected to the experiment, but are instead subjected to a defined set of parameters, or the controls are based on pre- or post-treatment levels.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. General

SOCS Proteins and Cytokine-Induced Signaling

Inflammation is the major mechanism of diseases caused by a multitude of biologic, chemical, and physical agents. The production of inflammatory mediators depends on a tightly regulated intracellular signaling by stress-responsive transcription factors as positive activators of the proinflammatory genetic program (Hawiger, J. Immunol. Res. (2001). Concurrently, genes that encode negative regulators of proinflammatory signaling, designated suppressors of cytolcine signaling (SOCS), are also activated to limit the magnitude and/or duration of an inflammatory response during naturally occurring infections (Alexander, W. S. Nat Rev Immunol 2:410-6 (2002)). On a molecular level, closely related members of the SOCS family, SOCS1 and SOCS3, block phosphorylation-dependent activation of STAT1 (signal transducer and activator of transcription 1) in response to interferon gamma (IFN-γ) and target the IFN-γ receptor signaling complex for proteosomal degradation (Krebs, D. L. & Hilton, D. J. J Cell Sci 113(Pt 16): 2813-9 (2000), Krebs, D. L. & Hilton, D. J. Stem Cells 19: 378-87 (2001), Yasukawa et al. Annu Rev Immunol 18:143-64 (2000), Zhang, J. G. et al. Proc Natl Acad Sci USA 98:13261-5 (2001)). Conditional deficiency of SOCS3 in mouse macrophages renders them susceptible to proinflammatory agonists clearly demonstrating its ability to suppress excessive inflammatory signaling at the cellular level (Yasukawa, H. et al. Nat Immunol 4:551-6 (2003); Lang, R. et al. Nat Immunol 4:546-50 (2003), Croker, B. A. et al. Nat Immunol 4:540-5 (2003)).

Despite the presence of negative regulators such as SOCS, the host defense systems remain susceptible to runaway systemic inflammatory responses. For example, staphylococcal and streptococcal superantigens robustly activate T cells, resulting in tissue injury and death (Balaban et al. Int J Food Microbiol 64, 33-40 (2001), Dinges et al. Clin Microbiol Rev 13, 16-34, (2000)). Staphylococcal enterotoxin B (SEB), for example, induces non-menstrual toxic shock syndrome (NMTSS) in humans and a fatal respiratory distress syndrome in non-human primates (Balaban et al. Int J Food Microbiol 64, 33-40 (2001), Mattix et al. Toxicol Pathol 23, 262-8 (1995)). These characteristics of SEB are important not only for its potential use as a bioweapon (Madsen et al. Clin Lab Med 21, 593-605 (2001)) but also as a virulence factor in community-acquired staphylococcal infections caused by antibiotic-resistant strains, which currently exceed two million annually in the United States (Fey et al. Antimicrob Agents Chemother 47, 196-203 (2003); Clark et al. Curr Opin Crit. Care 9, 403-12 (2003)). NMTSS is characterized by uncontrolled production of inflammatory cytolines and chemokines that contribute to widespread tissue injury, multiple organ failure, collapse of vascular system, and death.

Example 4 shows intracellular protein therapy in acute systemic inflammation elicited by SEB and related superantigens that target T cells. In the SEB toxicity model employed in Example 4, intraperitoneal administration of CP-SOCS3 resulted in its intracellular persistence in blood and spleen leukocytes and lymphocytes, a suppression of IL-6 and MHC class II expression, and the prevention of the severe liver injury manifested by apoptosis and hemorrhagic necrosis. Cumulatively, CP-SOCS3 dramatically improved the survival of SEB-challenged mice.

Apoptotic and hemorrhagic injury in mouse liver was suppressed in vivo (Example 5) and the survival of mice after SEB challenge was increased strikingly by CP-SOCS3 proteins. These in vivo results indicate that endogenously expressed SOCS proteins are insufficient to stem the massive inflammatory insult by a bewildering array of cytokines and chemokines during acute systemic inflammation unleashed by SEB and related superantigens. However, the supply of exogenous CP-SOCS3 is sufficient to suppress signaling in vivo. In vivo delivery of CP-SOCS3 was fast, reaching the highest level of detection in blood leulocytes and lymphocytes 1 hour after intraperitoneal injection and somewhat later (2 hours) in the spleen. Importantly, CP-SOCS3 persisted in blood cells and spleen for at least 8 hours following a single intraperitoneal injection. These data contribute to a better understanding of the mechanism of in vivo action of CP-SOCS3 by linking its persistence to the suppression of IL-6 and MHC-II induction and the striking gain in survival at 72 hours. These findings support the use of an intracellular replacement therapy to replenish endogenously low levels of SOC proteins. By providing a sufficient supply of exogenous CP-SOCS3, the state of unresponsiveness to the deleterious effects of excessive cytokine signaling is maintained. The observed in vivo persistence of administered CP-SOCS3 for at least 8 hours reflects the capacity of this recombinant, cell-penetrating protein to escape from rapid intracellular degradation observed with endogenous SOCS3 (Rui et al. *J Biol Chem* 277: 42394-8(2002)).

Intracellular protein therapy can be based on engineering cell-penetrating proteins that contain membrane-translocating motif (MTM) derived from hydrophobic region of signal sequence that has been conserved through evolution (Veach et al. *J Biol Chem* 279:11425-31 (2004), Hawiger, *J Curr Opin Immunol* 9:189-94 (1997)). By using signal sequence hydrophobic region, endosomal sequestration of recombinant SOCS3 can be avoided thereby allowing its unrestricted intracellular and intercellular trafficking. Such trafficking is required for in vivo delivery and intracellular targeting in multiple cell types involved in inflammation. It was also established that two CP-SOCS3 proteins reduced the production of IL-6 and suppressed the inducible cell-surface expression of MHC class II molecules in macrophages analyzed in SEB-challenged mice. Given a critical role of IFN-γ in induction of MHC-II, inhibition of STAT1 phosphorylation necessary for the activation of CIITA promoter IV and the subsequent expression of MHC class II molecules was achieved.

In addition to SEB, other bacterial superantigens, unrelated toxins, viruses, and chemical agents are known to induce inflammation of the vital organs. These inflammation-based systemic diseases can be amenable to treatment with CP-SOCS3. Moreover, intestinal inflammation and arthritis can be controlled by genetic manipulations or gene therapy-based approaches such as the induction of SOCS3 or delivery of SOCS3 using adenoviral vectors, respectively (Shouda et al. *J Clin Invest* 108:1781-8 (2001), Suzuki et al. *J Exp Med* 193:471-81 (2001)).

C. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular SOCS sequence is disclosed and discussed and a number of modifications that can be made to a number of molecules are discussed, specifically contemplated is each and every combination and permutation of the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Disclosed herein are isolated polypeptides comprising a suppressor of cytokine signaling (SOCS) sequence and a membrane translocating motif (MTM) sequence. Such polypeptides can be referred to as "cell-penetrating SOCS polypeptides" or "cell-penetrating SOCS sequences." Any SOCS protein, such as SOCS-1, SOCS-2, SOCS-3, SOCS-4, SOCS-5, SOCS-6, or SOCS-7 (or fragment thereof), from any species, in any combination, can be used as the source of the SOCS sequence. The SOCS protein(s) used can be selected based on the purpose to be accomplished by importing the molecule into the selected cell. Also contemplated are isolated nucleic acid encoding a polypeptide comprising a SOCS sequence and a membrane translocation sequence. Such nucleic acid sequences can be referred to as "cell-penetrating SOCS nucleic acids." Also disclosed are vectors and cells comprising the cell-penetrating SOCS nucleic acids. The SOCS sequence can comprise a SOCS protein.

SOCS proteins have a central SH2 domain and relatively well-preserved amino acid sequences that form the SOCS box or CIS homology (CH) domain. SOCS1 and SOCS3 also have unique 30 amino acid residues at the N-terminal side of the SH2 domain, named the kinase inhibitory region (KIR). The SOCS sequences disclosed herein can comprise all or a functional part of SH2, kinase inhibition, and SOCS-box domains of SOCS proteins individually or in any combination. Therefore, herein contemplated are SOCS sequences comprising all or a functional part of an SH2 domain, a KIR domain, or a SOCS box domain of a SOCS protein. Also contemplated are SOCS sequences comprising all or a functional part of SH2 and KIR domains, SH2 and SOCS box domains, or KIR and SOCS box domains. Also contemplated are all three domains together: all or a functional part of SH2, KIR, and SOCS-box domains. By "functional part" is meant a part, portion or segment of the domain that retains the suppression of cytokine signaling function either alone or in combination with other SOCS protein domains or parts of domains.

"SOCS sequence" can also be defined functionally. Cytokine signaling induces the expression of SOCS proteins through the JAK-STAT signaling pathway. The induced SOCS proteins block the interaction of STATs with receptors by steric hindrance or competition via SH2-domain-mediated binding to JAKs and cytokine receptors; or inhibit the catalytic activity of JAKs though binding via the KIR and SH2 region. Therefore, "SOCS sequence" as used herein can also be defined as being any amino acid sequence capable of functioning as a suppressor of cytokine signaling. Such suppression can be defined as a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% suppression of cytokine signaling. This suppression can be measured by measuring expansion of lymphoid progenitors, STAT5 phosphorylation, or expression of TNF-α, IL-6, and other cytokines. Examples of measuring suppression can be found, for example, in Alexander et al. (Annu. Rev. Immunol. (2004) 22:503-29) and Alexander et al. (Nat. Rev. Immun. (2002) 2:1-7), both herein incorporated by reference in their entirety for their teaching regarding measuring suppression of intracellular signaling induced by cytokines and growth factors. Alternatively, full-length SOCS proteins or their fragments can contain one or more mutated residues rendering them dominant negative inhibitors of endogenous SOCS proteins. Such inhibitors can prevent SOCS proteins from extinguishing physiologic signaling evoked by growth factors and hormones (examples include reversal of anemia during chronic infection or reversal of insulin and leptin resistance in metabolic syndrome that characterizes type II diabetes) An example of a full-length SOCS-1 amino acid sequence is provided herein as SEQ ID NO:3. Nucleic acid sequences encoding this amino acid sequence are also provided herein. The amino acid sequence of human SOCS-1 as well as a nucleic acid encoding human SOCS-1 (SEQ ID NO:18) can be accessed via GenBank under Accession No. NM_003745. The sequences and all information disclosed under Accession No. NM_003745 are incorporated herein in their entirety by this reference. The amino acid sequence of mouse SOCS-1 (SEQ ID NO:25) as well as a nucleic acid encoding mouse SOCS-1 (SEQ ID NO:26) can be accessed via GenBank under Accession No. NM_009896. The sequences and all information disclosed under Accession No. NM_009896 are incorporated herein in their entirety by this reference.

Also disclosed are mutated SOCS proteins and mutated SOCS sequences, which can be used in the disclosed compositions and methods in place of or in addition to the SOCS sequence. However, as used herein, the terms SOCS protein and SOCS sequence do not encompass mutated SOCS protein or mutated SOCS sequence unless the context indicates otherwise. Useful mutated SOCS proteins and sequences lack or have reduced suppressor of cytokine signaling function. The lack or reduction in this function can be determined using techniques described elsewhere herein for determining suppressor of cytokine signaling function.

An example of a full length SOCS-2 amino acid is provided herein as SEQ ID NO:20. The amino acid sequence of human SOCS-2 as well as a nucleic acid encoding human SOCS-2 (SEQ ID NO:23) can be accessed via GenBank under Accession No. NM_003877. The sequences and all information disclosed under Accession No. NM_003877 are incorporated herein in their entirety by this reference. The amino acid sequence of mouse SOCS-2 (SEQ ID NO:12) as well as a nucleic acid encoding mouse SOCS-2 (SEQ ID NO:10) can be accessed via GenBank under Accession No. NM_007706. The sequences and all information disclosed under Accession No. NM_007706 are incorporated herein in their entirety by this reference.

An example of a full-length SOCS-3 amino acid sequence is provided herein as SEQ ID NO:4. Nucleic acid sequences encoding this amino acid sequence are also provided herein. The amino acid sequence of human SOCS 3 as well as a nucleic acid encoding human SOCS-3 (SEQ ID NO: 11) can be accessed via GenBank under Accession No. NM_003955. The sequences and all information disclosed under Accession No. NM_003955 are incorporated herein in their entirety by this reference. The amino acid sequence of mouse SOCS-3 (SEQ ID NO:24) as well as a nucleic acid encoding mouse SOCS-3 (SEQ ID NO: 13) can be accessed via GenBank under Accession No. NM_007707. The sequences and all information disclosed under Accession No. NM_007707 are incorporated herein in their entirety by this reference. Fragment of the sequences disclosed herein can be combined with an appropriate membrane translocation sequence or signal peptide to make the disclosed cell-penetrating SOCS polypeptides.

As described above, the isolated polypeptide comprising a SOCS sequence can also comprise a "membrane translocating motif", also referred to herein and known as "importation competent signal peptide" or "cell membrane-permeable hydrophobic region of a signal peptide." As used herein, a membrane translocating motif is a sequence of amino acids that they have a hydrophobic, lipid-soluble portion. Membrane translocating motifs generally can have a length of about 10 to about 25 or more amino acid residues, many residues of which (typically about 55-60%) are hydrophobic. The hydrophobic portion is a common, major motif of signal peptides, and it is often a central part of the signal peptide of protein secreted from cells. Thus, signal peptides are useful forms of the disclosed membrane translocating motif or a useful source of sequences, such as sequences constituting the hydrophobic portion of a signal sequence, for use in the disclosed membrane translocation sequence. A signal peptide is a peptide capable of penetrating through the endoplasmic reticulum membrane to allow the export of cellular proteins. Signal peptides for use in and with the disclosed compositions and methods are also "importation competent" or "cell-permeant," i.e., capable of penetrating through the cell membrane from outside the cell to the interior of the cell. Amino acid residues of membrane translocating motifs and signal peptides can be mutated and/or modified (i.e., to form mimetics) so long as the modifications do not affect the translocation-mediating function of the membrane translocating motifs and signal peptides. Thus the words "motif" and "peptide" include mimetics and the word "amino acid" includes modified amino acids, as used herein, unusual amino acids, and D-form amino acids. Importation competent signal peptides for use in and with the disclosed compositions and methods have the function of mediating translocation across a cell membrane from outside the cell to the interior of the cell and vice versa. Such importation competent signal peptides can be modified such that they lose the ability to export a protein but maintain the ability to import molecules into a cell.

Signal peptides for use as, or as a source for sequences in, membrane translocation sequences can be selected, for example, from the SIGPEP database (http://proline.bic.nus.edu.sg/sigpep), which also lists the origin of the signal peptide. When a specific cell type is to be targeted, a signal peptide used by that cell type can (but need not) be chosen. For example, signal peptides encoded by a particular oncogene can be selected for use in targeting cells in which the oncogene is expressed. Additionally, signal peptides endogenous to the cell type can be chosen for importing biologically active molecules into that cell type. And again, any selected membrane translocating motif, signal peptide, or derivative thereof can be routinely tested for the ability to translocate across the cell membrane of any given cell type according to the teachings herein. Specifically, for example, the signal peptide of choice can be conjugated to a SOCS sequence, SOCS protein, or marker protein and administered to a cell, and the cell can be subsequently screened for the presence of the active molecule or marker protein. One useful form of hydrophobic region of a membrane translocation sequence can be the membrane translocating motif (MTM) of FGF-4. For example, the hydrophobic region can be the amino acid sequence provided herein as SEQ ID NO: 2 (AAVLLPVL-LAAP). SEQ ID NO: 2 is the hydrophobic region of the membrane translocation sequence utilized in the Examples to make SOCS-1 and SOCS-3 fusion proteins.

The disclosed SOCS sequences can also be administered as a complex with a membrane translocating motif. Such a complex can further comprise a liposome. Cationic and anionic liposomes are contemplated, as well as liposomes having neutral lipids. Cationic liposomes can be complexed with the membrane translocating motif and a negatively-charged SOCS sequence by mixing these components and allowing them to charge-associate. Examples of cationic liposomes include lipofectin, lipofectamine, lipofectace and DOTAP. Anionic liposomes generally are utilized to encase within the liposome the substances to be delivered to the cell. Procedures for forming cationic liposomes encasing substances are standard in the art and can readily be utilized herein by one of ordinary skill in the art to encase the disclosed cell-permeable SOCS polypeptides, SOCS sequences, and SOCS complexes.

Any selected cell into which import of a biologically active molecule would be useful can be targeted by this method, as long as there is a means to bring the disclosed cell-penetrating SOCS polypeptides, SOCS sequences, and SOCS complexes into contact with the selected cell. Cells can be within a tissue or organ, for example, supplied by a blood vessel into which the SOCS polypeptide, sequence or complex is administered. Additionally, the cell can be targeted by, for example, inhalation of the SOCS polypeptide, sequence or complex containing membrane translocating motif linked to a peptide to target the lung epithelium. Some examples of cells that can be targeted by this method include fibroblasts, epithelial cells, endothelial cells, blood cells and tumor cells, among many. In addition, the SOCS polypeptide, sequence or complex can be administered directly to a tissue site in the body. As discussed above, the membrane translocating motif utilized can be chosen from, for example, signal peptides known to be utilized by the selected target cell, or a desired signal peptide can be tested for importing ability given the teachings herein. An example of testing the importation ability of a membrane translocating motif is disclosed in Example 2 and Example 3, in which fluorescein isothiocyanate (FITC) is used. Generally, however, all signal peptides have the common ability to cross cell membranes due, at least in part, to their hydrophobic character. Thus, in general, a membrane translocating motif can be designed and used for any cell type, since all eukaryotic cell membranes comprise a common lipid bilayer.

The isolated polypeptide comprising a SOCS sequence can also contain a sequence for affinity purification. Such sequences can be referred to as "purification sequences." Examples of such sequences include, but are not limited to polyhistidine tags, Protein A (Pharmacia Biotech) Protein Z (Pharmacia Biotech), ABP, GST (Pharmacia Biotech), MBP (New England Biolabs), FLAG peptide (Kodak), and Pin-Pointe (Promega) and TAP tag (Drakas R et al. Proteomics 5:132 (2005).

Also disclosed herein are CP-SOCS fusion proteins His-SOCS-3 (SEQ ID NO: 18), HS3M (SEQ ID NO: 19), His-SOCS3-MTM (SEQ ID NO: 20), and HMS3 SEQ ID NO: 21).

1. Homology/Identity

It is understood that one way to define any known variants and derivatives or those that might arise, of the disclosed genes and proteins herein is through defining the variants and derivatives in terms of homology to specific known sequences. For example SEQ ID NO:23 sets forth a particular sequence of nucleic acid, and SEQ ID NO:20 sets forth a particular sequence of the protein encoded by SEQ ID NO:23, a SOCS protein. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.) or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

2. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods can differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

3. Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization can involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

4. Nucleic Acids

There are a variety of molecules disclosed herein that are nucleic acid based, including for example the nucleic acids that encode, for example, SOCS sequences as well as any other proteins disclosed herein, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Other types of molecules (conjugates) to can be linked to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556), A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Sequences

There are a variety of sequences related to, for example, SOCS, as well as any other protein disclosed herein that are disclosed on Genbank, and these sequences and others are herein incorporated by reference in their entireties as well as for individual subsequences contained therein.

A variety of sequences are provided herein and these and others can be found in Genbank, at www.pubmed.gov. Those of skill in the art understand how to resolve sequence discrepancies and differences and to adjust the compositions and methods relating to a particular sequence to other related sequences. Primers and/or probes can be designed for any sequence given the information disclosed herein and known in the art.

c) Primers and Probes

Disclosed are compositions including primers and probes, which are capable of interacting with the genes disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the nucleic acid or region of the nucleic acid or they hybridize with the complement of the nucleic acid or complement of a region of the nucleic acid.

d) In vivo/ex vivo

As described above, the compositions can be administered in a pharmaceutically acceptable carrier and can be delivered to the subject's cells in vivo and/or ex vivo by a variety of mechanisms well known in the art. If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

5. Peptides a) Protein Variants

As discussed herein there are numerous variants of SOCS proteins, such as those found in SEQ ID NOS:3, 4, 12, 20, and 24, and SOCS sequences such as those found in SEQ ID NOS:7-9 and 19, 21, and 22, that are known and herein contemplated. In addition to the known functional SOCS variants, derivatives of the SOCS proteins can also function in the disclosed methods and compositions. Protein variants and derivatives are well understood to those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations |
|---|---|
| alanine | Ala, A |
| allosoleucine | AIle |
| arginine | Arg, R |
| asparagine | Asn, N |
| aspartic acid | Asp, D |
| cysteine | Cys, C |
| glutamic acid | Glu, E |
| glutamine | Gln, K |
| glycine | Gly, G |
| histidine | His, H |
| isolelucine | Ile, I |
| leucine | Leu, L |
| lysine | Lys, K |
| phenylalanine | Phe, F |
| proline | Pro, P |
| pyroglutamic acidp | Glu |
| serine | Ser, S |
| threonine | Thr, T |
| tyrosine | Tyr, Y |
| tryptophan | Trp, W |
| valine | Val, V |

TABLE 2

Amino Acid Substitutions
Original Residue Exemplary Conservative Substitutions,
others are known in the art.

ala; ser
arg; lys; gln
asn; gln; his
asp; glu
cys; ser
gln; asn; lys
glu; asp
gly; pro
his; asn; gln
ile; leu; val
leu; ile; val
lys; arg; gln;
met; leu; ile
phe; met; leu; tyr
ser; thr
thr; ser
trp; tyr
tyr; trp; phe
val; ile; leu Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also can be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the protein sequence set forth in SEQ ID NO:4 is set forth in SEQ ID NO:11. It is understood that while no amino acid sequence indicates what particular DNA sequence encodes that protein within an organism, where particular variants of a disclosed protein are disclosed herein, the known nucleic acid sequence that encodes that protein in the particular sequence from which that protein arises is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH=CH—(cis and trans), —$COCH_2$—, —CH(OH)$CH_2$—, and —$CHH_2SO$—(These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—CH $H_2$—S); Hann J. Chem. Soc Perkin Trans. 1307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—CH(OH)$CH_2$—); Holladay et al. Tetrahedron. Lett 24:4401-4404 (1983) (—C (OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

6. Pharmaceutical Carriers/Delivery of Pharmaceutical Products

Suitable import conditions are exemplified herein and include cell and SOCS polypeptide, sequence or complex temperature between about 180° C. and about 42° C., with a preferred temperature being between about 22° C. and about 37° C. For administration to a cell in a subject the SOCS polypeptide, sequence or complex, once in the subject, will of course adjust to the subject's body temperature. For ex vivo administration, the SOCS polypeptide, sequence or complex can be administered by any standard methods that would maintain viability of the cells, such as by adding it to culture medium (appropriate for the target cells) and adding this medium directly to the cells. As is known in the art, any medium used in this method can be aqueous and non-toxic so as not to render the cells non-viable. In addition, it can contain standard nutrients for maintaining viability of cells, if desired. For in vivo administration, the SOCS polypeptide, sequence or complex can be added to, for example, a blood sample or a tissue sample from the patient or to a pharmaceutically acceptable carrier, e.g., saline and buffered saline, and administered by any of several means known in the art. Examples of administration include parenteral administration, e.g., by intravenous injection including regional perfusion through a blood vessel supplying the tissues(s) or organ(s) having the target cell(s), or by inhalation of an aerosol, subcutaneous or intramuscular injection, topical administration such as to skin wounds and lesions, direct transfection into, e.g., bone marrow cells prepared for transplantation and subsequent transplantation into the subject, and direct transfection into an organ that is subsequently transplanted into the subject. Further administration methods include oral administration, particularly when the SOCS polypeptide, sequence or complex is encapsulated, or rectal administration, particularly when the SOCS polypeptide, sequence or complex is in suppository form. A pharmaceutically acceptable carrier includes any material that is not biologically or otherwise undesirable, i.e., the material can be administered to an individual along with the selected SOCS polypeptide, sequence or complex without causing any undesirable biological effects or interacting in a deleterious manner with any of the other components of the pharmaceutical composition in which it is administered. Administration can be performed for a time length of about 1 minute to about 72 hours. Preferable time lengths are about 5 minutes to about 48 hours, and even more preferably about 5 minutes to about 20 hours, and even more preferably about 5 minutes to about 2 hours. Optimal time lengths and conditions for any specific SOCS polypeptide, sequence complex and any specific target cell can readily be determined, given the teachings herein and knowledge in the art.[27] Specifically, if a particular cell type in vivo is to be targeted, for example, by regional perfusion of an organ or tumor, cells from the target tissue can be biopsied and optimal dosages for import of the SOCS polypeptide, sequence or complex into that tissue can be determined in vitro, as described herein and as known in the art, to optimize the in vivo dosage, including concentration and time length. Alternatively, culture cells of the same cell type can also be used to optimize the dosage for the target cells in vivo.

As described above, the compositions can be administered in vivo in a pharmaceutically acceptable carrier. By "pharmaceutically acceptable" is meant a material that is not biologically or otherwise undesirable, i.e., the material can be administered to a subject, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions can be administered orally, parenterally (e.g., intravenously), by intramuscular injection, by intraarterial injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews,* 129: 57-80, (1992); and Roffier, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed compositions can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions can be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. A typical daily dosage of a SOCS sequence or a cell-penetrating SOCS sequence can range from about 1 µg/kg to up to 100 mg/kg of body weight or more per day, depending on the factors mentioned above.

Following administration of a disclosed composition, such as SOCS sequences or a cell-penetrating SOCS sequences, for treating, inhibiting, or preventing inflammation, for example, the efficacy of the therapeutic antibody can be assessed in various ways well known to the skilled practitioner. For instance, one of ordinary skill in the art will understand that a composition, such as a polypeptide, disclosed herein is efficacious in treating or inhibiting inflammation in a subject by observing that the composition reduces the inflammation or prevents a further increase in inflammation.

The compositions that inhibit cytokine-induced signalling disclosed herein can be administered prophylactically to patients or subjects who are at risk for inflammation or who have been newly exposed to an inflammation inducing substance, such as bacteria.

Other molecules that interact with SOCS to inhibit inflammation which do not have a specific pharmaceutical function, but which may be used for tracking changes within cellular chromosomes or for the delivery of diagnostic tools for example can be delivered in ways similar to those described for the pharmaceutical products.

The disclosed compositions and methods can also be used for example as tools to isolate and test new drug candidates for a variety of inflammation related diseases.

7. Chips and Micro Arrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

8. Computer Readable Mediums

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

9. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include the disclosed cell-penetrating SOCS polypeptides, as well as the buffers and enzymes required to use the polypeptides as intended. For example, disclosed is a kit for treating inflammation in a subject comprising a pharmaceutical composition as disclosed herein.

10. Compositions with Similar Functions

It is understood that the compositions disclosed herein have certain functions, such as inhibition of cytokine induced signaling. Disclosed herein are certain structural requirements for performing the disclosed functions, and it is understood that there are a variety of structures which can perform the same function which are related to the disclosed structures, and that these structures will ultimately achieve the same result, for example inhibition of cytokines.

D. Methods of Making the Compositions

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual,* 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.,* 65:610-620 (1980), (phosphotriester method). Protein nucleic acid molecules can be made using known methods such as those described by Nielsen et al., *Bioconjug. Chem.* 5:3-7 (1994).

2. Peptide Synthesis

One method of producing the disclosed proteins, such as SEQ ID NO:20, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W. H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides can be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

3. Process Claims for Making the Compositions

Disclosed are processes for making the compositions as well as making the intermediates leading to the compositions. For example, disclosed are nucleic acids in SEQ ID NOs:10, 11, 13, 18, and 23. There are a variety of methods that can be used for making these compositions, such as synthetic chemical methods and standard molecular biology methods. It is understood that the methods of making these and the other disclosed compositions are specifically disclosed.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate.

Also disclose are animals produced by the process of adding to the animal any of the cells disclosed herein.

E. Methods of Using the Compositions

1. Methods of Using the Compositions as Research Tools

The disclosed compositions can be used in a variety of ways as research tools. For example, the disclosed compositions, such as SEQ ID NOs:3, 4, 7, 8, 12, 19, 21, 22 and 24 can be used to study the interactions between SOCS proteins or SOCS sequences and inflammatory reactions, by for example acting as inhibitors of binding.

The compositions can be used for example as targets in combinatorial chemistry protocols or other screening protocols to isolate molecules that possess desired functional properties related to SOCS proteins or SOCS sequences.

The disclosed compositions can also be used diagnostic tools related to diseases, such as toxic shock syndrome, for example.

The disclosed compositions can be used as discussed herein as either reagents in micro arrays or as reagents to probe or analyze existing microarrays. The disclosed compositions can be used in any known method for isolating or identifying single nucleotide polymorphisms. The compositions can also be used in any method for determining allelic analysis of, for example, SOCS proteins or SOCS sequences. The compositions can also be used in any known method of screening assays, related to chip/micro arrays. The compositions can also be used in any known way of using the computer readable embodiments of the disclosed compositions, for example, to study relatedness or to perform molecular modeling analysis related to the disclosed compositions.

2. Methods of Treatment

Also disclosed are methods of administering the polypeptides disclosed herein to a subject. The polypeptides can be administered to treat a variety of conditions, diseases, and disorders associated with inhibition of cytokine signaling. For example, infection and inflammation can be treated. Furthermore, the polypeptides can be used to prevent inflammation and infection in a subject at risk for such.

Also disclosed are methods of inhibiting a cytokine-induced response in a cell, comprising administering to the cell a polypeptide disclosed herein, such as cell-penetrating SOC polypeptides and SOCS sequences. Also disclosed are methods of inhibiting a cytokine-induced response in a subject, comprising administering to the subject a polypeptide disclosed herein, such as cell-penetrating SOC polypeptides and SOCS sequences.

Also disclosed are methods of inhibiting a cytokine-induced response in a cell, comprising administering to the cell a complex comprising the polypeptides disclosed herein, such as cell-penetrating SOC polypeptides and SOCS sequences. Also disclosed are methods of inhibiting a cytokine-induced response in a subject, comprising administering to the subject a complex comprising a polypeptide disclosed herein, such as cell-penetrating SOC polypeptides and SOCS sequences.

(a) Inflammation

Disclosed herein are methods of reducing the severity of inflammation in a subject. These methods include the steps of selecting a subject with inflammation or at risk for inflammation, and administering to the subject an effective amount of a SOCS sequence or a cell-penetrating SOCS sequence as disclosed herein.

Inflammation can be associated with a number of different diseases and disorders. Examples of inflammation include, but are not limited to, inflammation associated with hepatitis, inflammation associated with the lungs, liver, and/or the kidneys, heart, brain and meninges, and/or skin and inflammation associated with an infectious process. Inflammation can also be associated with liver toxicity, which can be associated in turn with cancer therapy, such as apoptosis induction or chemotherapy, or a combination of the two, for example. Liver toxicity can also be chemically induced by such substances as dioxin, acetaminophen, and ethanol (alcoholic hepatitis).

The inflammation can be associated with an inflammatory disease, as disclosed above. The inflammation can also be associated with cancer. Examples of types of cancer include, but are not limited to, lymphoma (Hodgkins and non-Hodgkins) B-cell lymphoma, T-cell lymphoma, leukemia such as myeloid leukemia and other types of leukemia, mycosis fungoide, carcinoma, adenocarcinoma, sarcoma, glioma, blastoma, neuroblastoma, plasmacytoma, histiocytoma, melanoma, adenoma, hypoxic tumour, myeloma, AIDS-related lymphoma or AIDS-related sarcoma, metastatic cancer, bladder cancer, brain cancer, nervous system cancer, squamous cell carcinoma of the head and neck, neuroblastoma, glioblastoma, ovarian cancer, skin cancer, liver cancer, squamous cell carcinomas of the mouth, throat, larynx, and lung, colon cancer, cervical cancer, breast cancer, cervical carcinoma, epithelial cancer, renal cancer, genitourinary cancer, pulmonary cancer, esophageal carcinoma, head and neck carcinoma, hematopoietic cancer, testicular cancer, colo-rectal cancer, prostatic cancer, and pancreatic cancer.

Activated Cells can Also be Treated at the Site of Inflammation. "Activated cells" are defined as cells that participate in the inflammatory response. Examples of such cells include, but are not limited to, T-cells and B-cells, macrophages, NK cells, mast cells, eosinophils, neutrophils, Kupffer cells, antigen presenting cells, as well as vascular endothelial cells.

(b) Infection

Inflammation can be associated with an infection, such as a viral or bacterial infection. In one example, the bacterial infection can be a *Staphlylococcus aureus* enterotoxin B-producing infection. The severity of infection in the subject can be reduced after treatment, as well as the severity of the symptoms of infection and inflammation. The polypeptide can be administered to the subject prior to or after surgery. The polypeptide can also be administered to the subject prior to or after contact with an infectious biological weapon.

When the inflammation is associated with an infectious process, the infectious process can be associated with a viral infection. Examples of viral infections include, but are not limited to, Herpes simplex virus type-1, Herpes simplex virus type-2, Cytomegalovirus, Epstein-Barr virus, Varicellazoster virus, Human herpesvirus 6, Human herpesvirus 7, Human herpesvirus 8, Variola virus, Vesicular stomatitis virus, Hepatitis A virus, Hepatitis B virus, Hepatitis C virus, Hepatitis D virus, Hepatitis E virus, Rhinovirus, Coronavirus including SARS viruses, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Norwalk virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human immunodeficiency virus type-1, and Human Immunodeficiency virus type-2. The infectious agent can also be a prion, such as those associated with bovine spongiform encephalitis, for example.

When the inflammation is associated with an infectious process, the infectious process can be associated with a bacterial infection. The bacterial infection can be caused by either gram positive or gram negative bacterium. The gram positive bacterium can be selected from the group consisting of: *M. tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus saprophyticus, Staphylococcus equi, Streptococcus pyogenes, Streptococcus agalactiae, Listeria monocytogenes, Listeria ivanovii, Bacillus anthracis, B. subtilis, Nocardia asteroides*, and other *Nocardia* species, *Streptococcus viridans* group, *Peptococcus* species, *Peptostreptococcus* species, *Actinoinyces israelii* and other *Actinomyces* species, and *Propionibacterium acnes*.

The gram negative bacterium can be selected from the group consisting of: *Clostridium tetani, Clostridium perfringens, Clostridium botulinum*, other *Clostridium* species, *Pseudomonas aeruginosa*, other *Pseudomonas* species, *Campylobacter* species, *Vibrio cholerae, Ehrlichia* species, *Actinobacillus pleuropneumoniae, Pasteurella haemolytica, Pasteurella multocida*, other *Pasteurella* species, *Legionella pneumophila*, other *Legionella* species, *Salmonella typhi*, other *Salmonella* species, *Shigella* species *Brucella abortus*, other *Brucella* species, *Chlamydi trachomatis, Chlamydia psittaci, Coxiella burnetti, Escherichia coli, Neiserria meningitidis, Neiserria gonorrhea, Haemophilus influenzae, Haemophilus ducreyi*, other *Hemophilus* species, *Yersinia pestis, Yersinia enterolitica*, other *Yersinia* species, *Escherichia coli, E. hirae* and other *Escherichia* species, as well as other *Enterobacteriacae, Brucella abortus* and other *Brucella* species, *Burkholderia cepacia, Burkholderia pseudomallei, Francisella tularensis, Bacteroides fragilis, Fusobascterium nucleatum, Provetella* species and *Cowdria ruminantium*.

The above examples of gram positive and gram negative bacteria are not intended to be limiting, but are intended to be representative of a larger population including all gram positive and gram negative bacteria, as well as non-gram test responsive bacteria. Examples of other species of bacteria include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Ainycolata, Ainycolatopsis, Anaerobospirillum, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacteriuin, Coxiella, Cryptobacterium, Delftia, Dermabacter, Dermatophilus, Desufomonas, Desulfovibrio, Dialister, Dichelobacter, Dolosicoccus, Dolosigranuluin, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacteriun, Mycoplasma, Myroides, Neisseria, Nocardia, Nocardiopsis, Ochrobactruin, Oeskovia, Oligella, Orientia, Paenibacillus, Pantoea, Parachlamydia, Pasteurella, Pediococcus, Peptococcus, Peptostreptococcus, Photobacterium, Photorhabdus, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia*, and *Yokenella*.

When the inflammation is associated with an infectious process, the infectious process can be associated with a parasitic infection. Examples of parasitic infections include, but are not limited to, *Toxoplasma gondii, Plasmodium* species such as *Plasmodium falciparum, Plasmodium vivax, Plasmodium malariae*, and other *Plasmodium* species, *Trypanosoma brucei, Trypanosoma cruzi, Leishmania* species such as *Leishmania major, Schistosoma* such as *Schistosoma mansoni* and other *Shistosoma* species, and *Entamoeba histolytica*.

When the inflammation is associated with an infectious process, the infectious process can be associated with a fungal infection. Examples of fungal infections include, but are not limited to, *Candida albicans, Cryptococcus neoformans, Histoplama capsulatum, Aspergillusfumigatus, Coccidiodes immitis, Paracoccidiodes brasiliensis, Blastomyces dermitidis, Pneomocystis carnii, Penicillium marneffi*, and *Alternaria alternata*.

(c) Biological Weapons

Disclosed herein are methods of reducing the severity of inflammation or infection in a subject prior to or after contact with an infectious agent such as a biological weapon. Biological warfare agents include, but are not limited to, bacteria, fungi, and viruses.

Examples of bacteria that can be used in biological warfare include *Bacillus anthracis* (Anthrax), *Chlamyida psittaci* (Ornithosis), *Rickettsia prowazeki* (typhus), *Vibrio cholerae* (Cholera) *Bartonella quintana* (Trench Fever) *Clostridium botulinum* (Botulism), *Rickettsia rickettsii* (Rocky Mountain Spotted Fever), *Yersinia pestis* (Plague), *Brucella melitensis* (Brucellosis), *Coxiella burnetti* (Q fever), *Rickettsia tsutsugamushii* (Scrub typhus), *Burkholderia mallei* (Glanders), *Francisella tulaensis* (Tularemia), *Salmonella typhi* (Typhoid), *Burkcholdera pseudomallei* (Meliodosis), *Rickettsia moonseri* (Typhus), *Staphylococcus enterotoxin B* (SEB) and *Shigella dysenteriae* (Dysentery).

Examples of fungi that can be used as biological warfare agents include, but are not limited to, *Coccidioides immitis* and *Histoplasma capsulatum*.

Examples of viruses that can be used as biological warfare agents include, but are not limited to, viral encephalitis agents, viral hemorrhagic fever agents, Chikungunya virus, Hantaan virus, Marburg virus, Tick-borne encephalitis virus, Congo-Crimean haemorrhagic fever virus, Japanese encephalitis virus, Monkey pox virus, Variola virus, Dengue fever virus, Junin virus, Omsk hemorrhagic fever virus, Venezuelan equine encephalitis virus, Eastern equine encephalitis virus, Lassa fever virus, Rift valley fever virus, Western equine encephalitis virus, Ebola virus, Lymphocytic choriomeningitis virus, Russian Spring-Summer encephalitis virus, White pox, Equine morbillivirus, Machupo virus, Smallpox virus, and Yellow fever virus.

The polypeptides disclosed herein can be administered to a subject at risk of exposure to a biological warfare agent. For example, the polypeptides can be administered to military troops or those at high risk of exposure to a biological warfare agent. The polypeptide can then prevent or reduce the severity of infection or inflammation in a subject. The polypeptides disclosed herein can be administered to a subject less than 1, 2, 3, 4, 5, 6, 12, 24, 36, or 48 hours, or more, prior to exposure. The polypeptides can also be administered to a subject after the subject has been exposed to a biological warfare weapon. The polypeptides can also be administered to the subject less than 1, 2, 3, 4, 5, 6, 12, 24, 36, or 48 hours, or more, after exposure. When the subject has been exposed prior to treatment, the subject should be treated as quickly as possible after exposure. The polypeptides disclosed herein can be administered in a variety of ways, as disclosed.

(d) Biological Systems

Also disclosed is a method comprising administering the polypeptide disclosed herein to a biological system. The biological system can be an inflamed biological system or a biological system at risk for inflammation. The severity of inflammation the biological system can be reduced.

The biological system can comprise an in vitro or ex vivo culture system. If the system comprises an in vitro culture, the culture can be used for screening, for diagnostic purposes, or for the preservation of biological materials. If an in vitro culture system is used, the disclosed compositions can be delivered to any type of cell. For example, they can be delivered to any type of mammalian cell. Exemplary types of cells neuron, glia, fibroblast, chondrocyte, osteocyte, endothelial, and hepatocyte.

Biological preservation of organs, tissues and cells are employed in many clinical and veterinary applications wherein living material, is harvested and stored in vitro for some period of time before use. Examples of such applications include organ storage and transplants, autologous and allogeneic bone marrow transplants, whole blood transplants, platelet transplants, cord blood and other stem cell transplants, embryo transfer, artificial insemination, in vitro fertilization, skin grafting and storage of tissue biopsies for diagnostic purposes. Preservation techniques are also important in the storage of cell lines for experimental use in hospital, industrial, university and other research laboratories.

If ex vivo methods are employed, cells or tissues can be removed and maintained outside the body according to standard protocols well known in the art. The biological system can comprise a tissue culture system or an organ culture system.

The polypeptides described herein can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type.

(e) Surgery and Transplantation

Disclosed herein are methods of reducing the severity of inflammation in a subject prior to or after surgery. Inflammation associated with surgery can be caused by an infection, for example. Infections associated with surgery are common, particularly during invasive procedures and those requiring implants, such as joint replacement surgery. Because the immune system is unable to attack bacteria that live on implants, infections can be a serious problem. If an infection of an implant goes untreated, the problem can worsen, and the bacteria can gain such a foothold that can become a systemic problem.

The polypeptides disclosed herein can be administered to a subject less than 1, 2, 3, 4, 5, 6, 12, 24, 36, or 48 hours, or more, prior to surgery. The polypeptides can also be administered to the subject less than 1, 2, 3, 4, 5, 6, 12, 24, 36, or 48 hours, or more, after surgery. The polypeptides can be administered to the subject in a variety of ways, as disclosed herein.

Disclosed are methods of reducing the risk of inflammation in a recipient of an implantation or a transplantation. Inflammation can be associated with transplant rejection in a transplant or implant recipient. As disclosed above, "transplant rejection" is defined as an immune response triggered by the presence of foreign blood or tissue in the body of a subject. In one example of transplant rejection, antibodies are formed against foreign antigens on the transplanted material. The transplantation can be, for example, tissue, cell or organ transplantation, such as liver, kidney, skin, corneal, pancreas, pancreatic islet cells, eyes, heart, or any other transplantable organ of the body.

Transplantation immunology refers to an extensive sequence of events that occurs after an allograft or a xenograft is removed from a donor and then transplanted into a recipient. Tissue is damaged at both the graft and the transplantation sites. An inflammatory reaction follows immediately, as does activation of biochemical cascades. Such as inflammatory reaction can be reduced using the methods taught herein. In the inflammatory reaction, a series of specific and nonspecific cellular responses ensues as antigens are recognized. Antigen-independent causes of tissue damage (i.e., ischemia, hypothermia, reperfusion injury) are the result of mechanical trauma as well as disruption of the blood supply as the graft is harvested. In contrast, antigen-dependent causes of tissue damage involve immune-mediated damage.

Macrophages release cytokines (e.g., tumor necrosis factor, interleukin-1), which heighten the intensity of inflammation by stimulating inflammatory endothelial responses; these endothelial changes help recruit large numbers of T cells to the transplantation site.

Damaged tissues release procoagulants (e.g., Tissue Factor and Hageman factor (factor XII) that trigger several biochemical cascades. The clotting cascade induces fibrin and several related fibrinopeptides, which promote local vascular permeability and attract neutrophils and macrophages. The kinin cascade principally produces bradykinin, which promotes vasodilation, smooth muscle contraction, and increased vascular permeability.

Rejection is the consequence of the recipient's alloimmune response to the nonself antigens expressed by donor tissues. In hyperacute rejection, transplant subjects are serologically presensitized to alloantigens (i.e., graft antigens are recognized as nonself). Histologically, numerous polymorphonuclear leukocytes (PMNs) exist within the graft vasculature and are associated with widespread microthrombin formation and platelet accumulation. Little or no leukocyte infiltration occurs. Hyperacute rejection manifests within minutes to hours of graft implantation. Hyperacute rejection has become relatively rare since the introduction of routine pretransplantation screening of graft recipients for antidonor antibodies.

In acute rejection, graft antigens are recognized by T cells; the resulting cytokine release eventually leads to tissue distortion, vascular insufficiency, and cell destruction. Histologically, leukocytes are present, dominated by equivalent numbers of macrophages and T cells within the interstitium. These processes can occur within 24 hours of transplantation and occur over a period of days to weeks.

In chronic rejection, pathologic tissue remodeling results from peritransplant and posttransplant trauma. Cytokines and tissue growth factor induce smooth muscle cells to proliferate, to migrate, and to produce new matrix material. Interstitial fibroblasts are also induced to produce collagen. Histologically, progressive neointimal formation occurs within large and medium arteries and, to a lesser extent, within veins of the graft. Leukocyte infiltration usually is mild or even absent. All these result in reduced blood flow, with subsequent regional tissue ischemia, fibrosis, and cell death. (Prescilla et al. http://www.emedicine.com, Immunology of Transplant Rejection, updated Jun. 20, 2003).

Transplant rejection may occur within 1-10 minutes of transplantation, or within 10 minutes to 1 hour of transplantation, or within 1 hour to 10 hours of transplantation, or within 10 hours to 24 hours of transplantation, within 24 hours to 48 hours of transplantation, within 48 hours to 1 month of transplantation, within 1 month to 1 year of transplantation, within 1 year to 5 years of transplantation, or even longer after transplantation.

The implant or transplant can be contacted with a SOCS sequence, cell-penetrating SOCS sequence, or SOCS protein. The implant or transplant can be contacted at least 1, 5, 10, 15, 20, 30, 45, or 60 minutes prior to implantation or transplantation. The implant or transplant can also be contacted at least 2, 3, 4, 5, 10, 12, 24, 36, or 48 hours prior to implantation or transplantation.

Chronic and subacute inflammation is linked to the development of obesity associated with insulin resistance, type 2 diabetes, and the metabolic syndrome. For example, insulin resistance has been linked to increased production of inflammatory cytokines (Hotamisligil, .G. S. Int. J. Obes 27, S53-55, (2003). Overproduction of a key proinflammatory cytokine, TNFα, is thought to contribute to insulin resistance in obesity (Uysal, K. T. et al Nature 389:610-614 (1997). TNFα and other proinflammatory cytokines induce expression of SOCS3 (Krebs, D. and Hilton D. J. Stems Cells 19:378-387 (2001). SOCS 3 attenuates insulin and leptin signaling (Emanuelli, B. et al J. Biol. Chem. 275, 15985-15991 (2000; Bjorbaek, C. et al. J. Biol. Chem. 274, 30059-30065).

A subject or cells obtained from a subject can be contacted with a mutated SOCS sequence, cell-penetrating mutated SOCS sequence, cell-penetrating mutated SOCS protein, a mutated SOCS3 sequence, cell-penetrating mutated SOCS3 sequence, cell-penetrating mutated SOCS3 protein or fragments thereof. These cell-penetrating mutated SOCS sequences, proteins or fragments act as inhibitors of endogenous SOCS (such as SOCS3) produced in response to chronic or subacute proinflammatory cytokine stimulation. Thus, its attenuating effect on insulin and leptin signaling are reversed. The type of SOCS protein (e.g., SOCS1, SOCS2) from which the mutated SOCS is derived generally will be the type of endogenous SOCS affected by administration of the mutated SOCS, but in some forms the mutated SOCS can affect other forms of endogenous SOCS.

F. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Optimization of Recombinant CP-SOCS3 Proteins

Recombinant, cell-penetrating murine SOCS3 proteins were designed and developed to encompass the entire amino acid sequence that consists of three functional segments: the N-terminal region with a kinase inhibitory activity, the SH2 domain, and the SOCS box (FIG. 1A). A membrane-translocating motif (MTM) comprised of 12 amino acids from a signal sequence hydrophobic region of Fibroblast Growth Factor 4 (Hawiger, J. Curr Opin Chem Biol 3:89-94 (1999) was attached to either the N-(HMS3) or C-(HS3M) terminal ends of SOCS3 to compare the impact of such positioning on the ability of recombinant SOCS3 to penetrate cells and exert its intracellular function. A control protein (HS3) lacking the MTM was also constructed to assess its requirement for cell penetration and intracellular function. Finally, all recombinant SOCS3 proteins contained a polyhistidine tag at the N-terminus to facilitate their purification (FIG. 1B). The purity of the three recombinant SOCS3 proteins was confirmed by SDS-PAGE analysis (FIG. 1C). The biological activities of purified soluble recombinant fusion proteins without (control) or with MTM were tested in cultured macrophages as well as the mouse model of SEB-induced inflammation and lethal apoptosis of the liver.

2. Example 2

Figure 2:
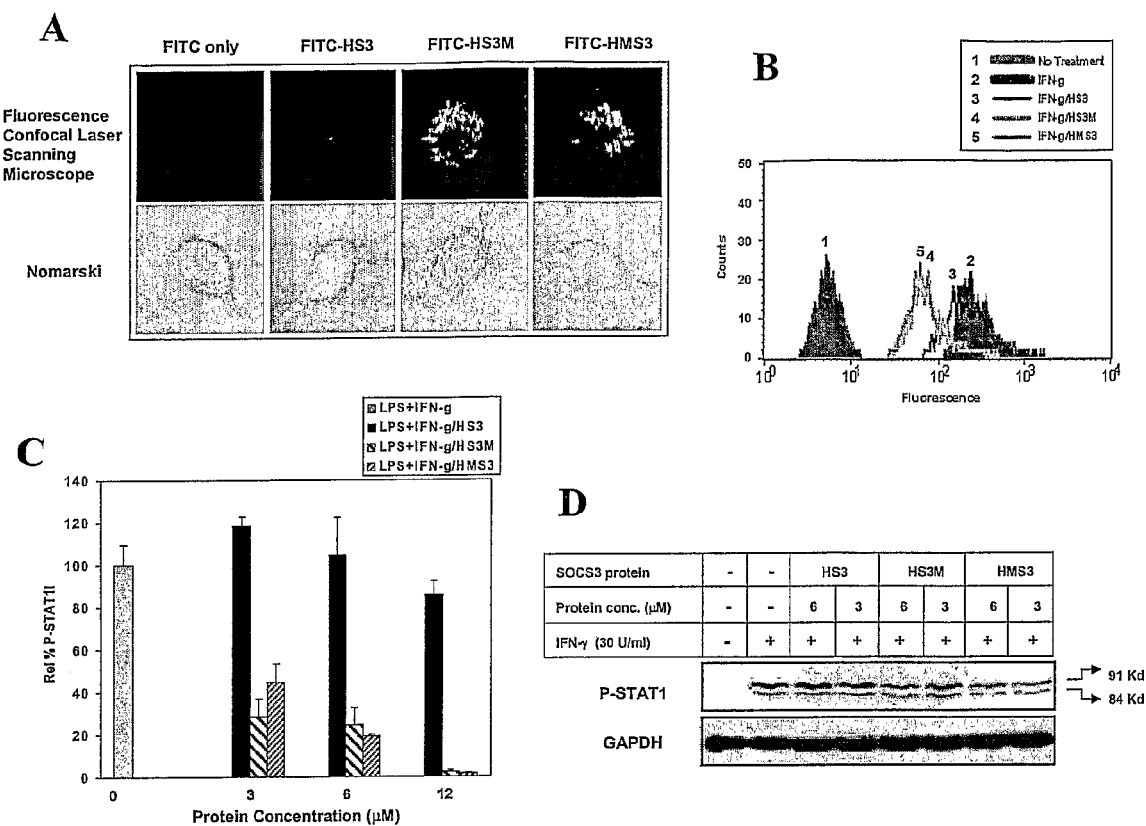
FIGS. 2A-2F show the intracellular delivery and inhibitory activity of CP-SOCS3 proteins toward phosphorylation of STAT1 and production of cytokines/chemokine in cultured macrophages.
Figure 2:
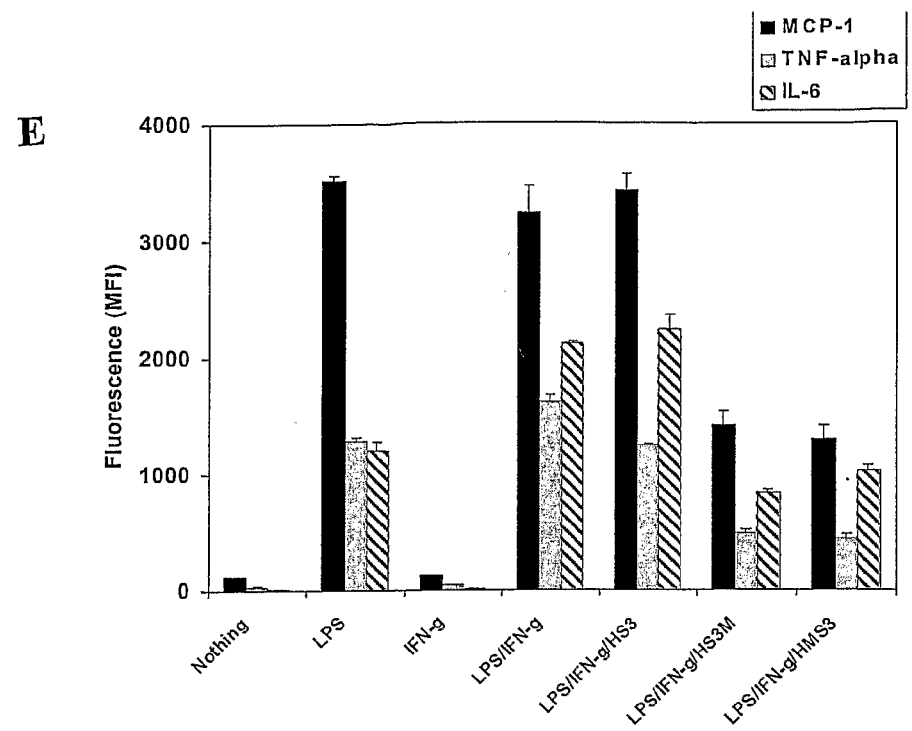
Figure 2:
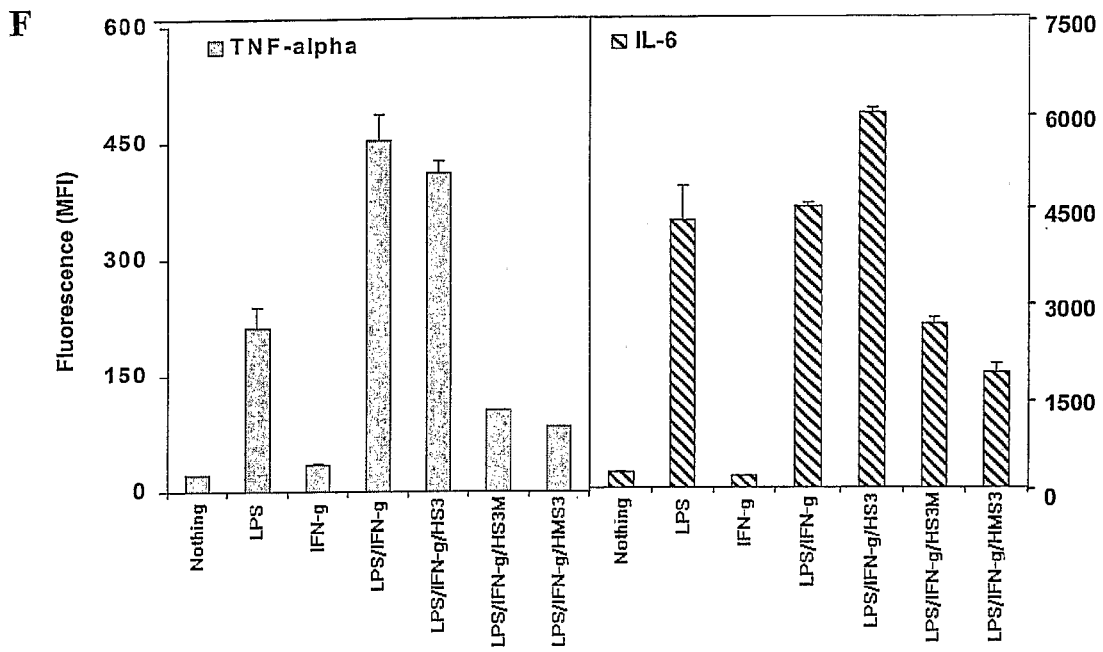

Intracellular Delivery and Effects of CP-SOCS3 on STAT1 Phosphorylation and Cytokine/Chemokine Production in Cultured Macrophages The intracellular delivery of recombinant SOCS3 proteins was detected in murine macrophage RAW cells by confocal laser scanning microscopy. Fluorescein isothiocyanate (FITC)-labeled SOCS3 lacking MTM was not detectable in RAW cells. In contrast, the two MTM-bearing SOCS3 proteins, HS3M and HMS3, were abundantly present in the cytoplasm of RAW cells (FIG. 2A). These cells were not fixed and the broad range protease, proteinase K, was used after pulsing cells with FITC-labeled proteins to prevent background fluorescence from cell surface-absorbed SOCS3 proteins. Thus, the protease-resistant fluorescence indicates that only MTM-bearing SOCS3 proteins exhibited their cell-penetrating capacity.

The ultimate test of cell-penetrating efficiency is a display of intracellular activity of SOCS3 proteins ferried by MTM. Inducibly-expressed endogenous SOCS 1 and 3 adaptor proteins are known to block STAT1 phosphorylation by Janus kinases (JAK) 1 and 2, a key step in intracellular signaling induced by IFN-γ (Krebs (2001), Yasukawa et al. (2003), Lang et al. (2003)). Using a quantitative and sensitive cytometric bead array (CBA) test, IFN-γ-induced phosphorylation of STAT1 was readily detected in cells exposed to control protein HS3, which lacks the MTM motif required for membrane penetration (FIG. 2B). In contrast, both forms of CP-SOCS3, HS3M and HMS3, suppressed STAT1 phosphorylation in a dose-dependent manner with IC50<3 μM (FIG. 2C). The inhibitory effect of CP-SOCS3 proteins on STAT1 phosphorylation was confirmed by immunoblotting studies, which revealed reduced levels of phosphorylated STAT1 and an alternatively spliced variant (91 kD and 84 kD) in whole cell lysates (FIG. 2D). The inhibitory effect of CP-SOCS toward STAT1 phosphorylation was selective because other stress-responsive transcription factors such as NF-κB, AP-1, and NFAT were not inhibited as determined by electrophoretic mobility gel shift assay of nuclear extracts of RAW cells treated with the proinflammatory agonist lipopolysaccharide (LPS) (data not shown). These transcription factors interact combinatorially with STAT1 when IFN-γ is used together with LPS to induce inflammatory cytokines (Lee, J. Y. & Sullivan, K. E. *Infect Immun* 69:2847-52 (2001)).

Inflammatory cytokines TNF-α and IL-6 were induced more robustly by a combination of LPS and IFN-γ as compared with either agonist alone (FIG. 2E). Notably, treatment of macrophages with 10 μM HS3M or HMS3 for one hour inhibited the expression of TNF-α, IL-6, and monocyte chemoattractant protein (MCP)-1 by 55-75% during subsequent 4 h incubation. In contrast, cytokines/chemokine expression in macrophages treated with a control non-cell penetrating HS3 protein was unchanged (FIG. 2E). Thus, two CP-SOCS3 proteins inhibited intracellular signaling evoked by a combination of two potent pro-inflammatory agonists, LPS and IFN-γ, as reflected by the suppression of cytokine and chemokine mediators of inflammation.

This analysis was extended to primary peritoneal macrophages isolated from C3H/HeJ mice. These mice have a point mutation in the Toll-like receptor 4 gene (tlr4) that makes them hyporesponsive to the LPS as compared to other strains such as Balb/C or C57/BL6 (Poltorak Science 282, 2085-8 (1998)). Although affinity-purified recombinant SOCS3 proteins contain relatively low amounts of LPS (8-13 μg/mg of purified protein), it was reasoned that LPS signaling through TLR4 pathway (Stoiber et al. *J Immunol* 163:2640-7 (1999) could augment the inhibitory effect of CP-SOCS3 by inducing the expression of an endogenous SOCS3. Therefore, primary macrophages from C3H/HeJ mice were used for these studies to obviate potentially confounding effects of trace amounts of LPS and to evaluate the sole effect of the recombinant proteins. Stimulation of primary macrophages with IFN-γ (100 U/ml) alone induced a low level of TNF-α expression (FIG. 2F). However, a much stronger TNF-α response was induced by a combination of IFN-γ and LPS (1 μg/ml) to couple IFN-γ signaling with alternative LPS pathway through TLR3 (Hoebe et al. *Nature* 424:743-8 (2003), Fitzgerald et al. *J Exp Med* 198:1043-55 (2003), Oshiumi et al. *J Biol Chem* 278:49751-62 (2003)). This pathway depends on interaction of TLR3 with adaptor protein Trif (lps2) (Hoebe et al. (2003), Fitzgerald et al. (2003)). Two CP-SOCS3 proteins suppressed TNF-α expression induced by LPS and IFN-γ combination in C3H/HeJ macrophages. Moreover, both CP-SOCS3 proteins inhibited production of IL-6 by 50 to 75%. In contrast, a control non-cell penetrating recombinant protein (HS3) was inactive (FIG. 2E, F). Thus, recombinant CP-SOCS3 proteins suppress an IFN-γ-primed and TLR4-independent signaling pathway induced in primary macrophages by interaction of LPS with TLR3 (Hoebe et al. (2003), Fitzgerald et al. (2003), Oshiumi et al. (2003)).

3. Example 3

In Vivo Tracking of CP-SOCS3 Intracellular Delivery

Figure 3:
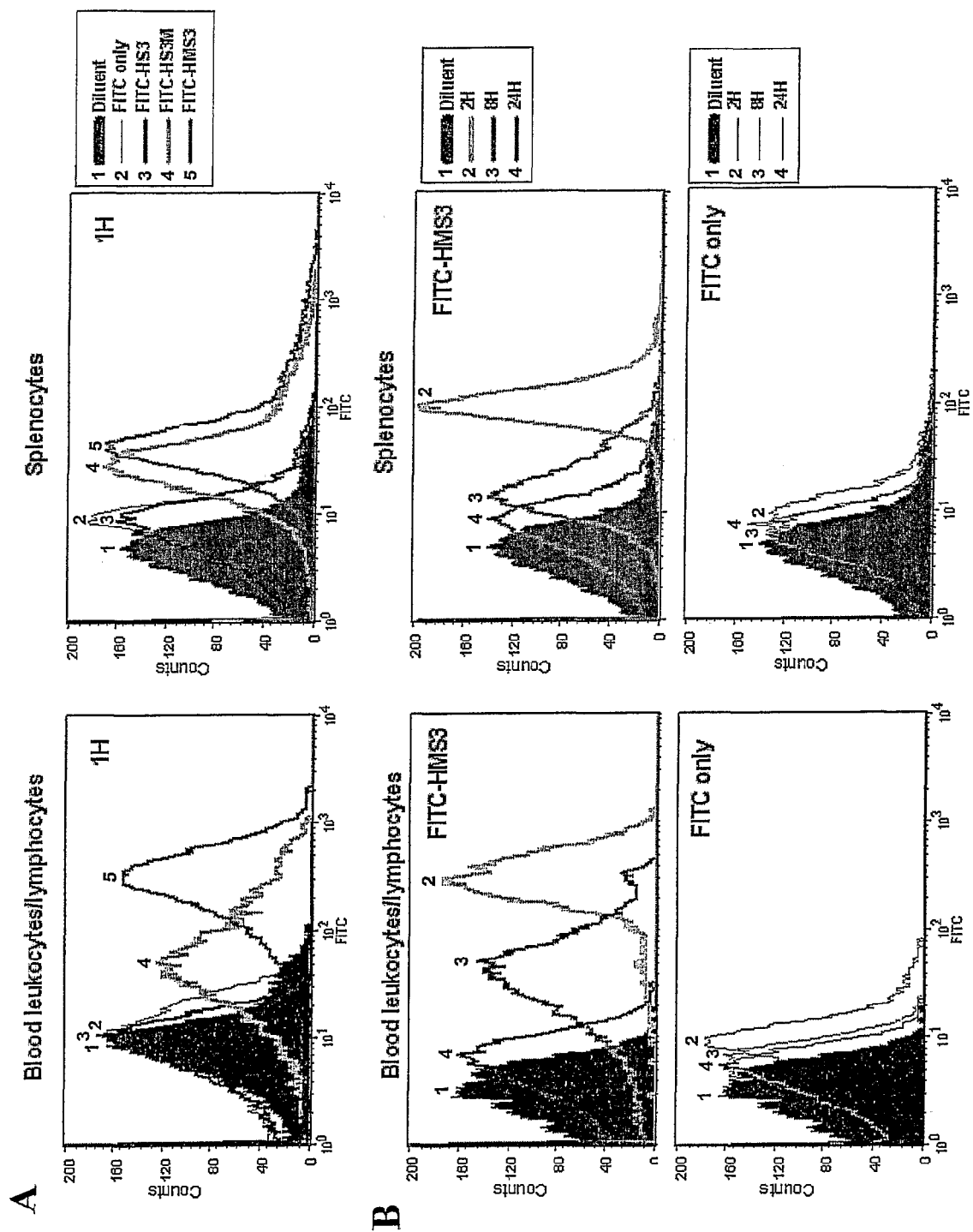
FIGS. 3A and 3B show in vivo delivery and intracellular persistence of the CP-SOCS3 proteins.

To monitor the in vivo delivery of CP-SOCS3 proteins, FITC-labeled HS3M and HMS3 were injected intraperitoneally into separate groups of C3H/HeJ mice. Peripheral blood leukocytes and lymphocytes, as well as those present in the spleen, were isolated at timed intervals and analyzed by flow cytometry following treatment with a broad range protease proteinase K to degrade FITC-labeled proteins absorbed on the cell membrane. The blood leukocyte/lymphocyte-rich fraction collected within 1 h of injection stained positive for the presence of FITC-labeled proteins as compared with controls that received FITC-labeled, non-cell penetrating HS3 or unconjugated FITC (FIG. 3A). One of two CP-SOCS3 proteins, HMS3, displayed a stronger intracellular signal in blood leukocytes/lymphocytes (FIG. 3A), lead to the analysis of its persistence in blood and spleen leukocytes/lymphocytes. Strikingly, FITC-labeled HMS3 was detectable, albeit in reduced amounts, at 8 h and even 24 h following intraperitoneal injection (FIG. 3B). In contrast, unconjugated free FITC at equimolar concentration (FITC only) failed to produce any significant gain in fluorescence as compared with diluent (FIG. 3B). Thus, MTM enabled two CP-SOCS3 proteins (HS3M and HMS3) to gain rapid (1 h) entry to blood and spleen leukocytes and lymphocytes wherein they persisted for at least 8 h.

4. Example 4

CP-SOCS3 Proteins Suppress Systemic Inflammatory Response Reflected by the Inhibition of IL-6 and MHC Class II Expression SEB induces T cell-dependent and cytokine-mediated systemic inflammation and fulminant liver injury followed by rapid death of D-galactosamine-sensitized mice (Miethke et al. *J Exp Med* 175: 91-8 (1992), Pfeffer, K. et al. *Cell* 73:457-67 (1993), Car, B. D. et al. *J Exp Med* 179:1437-44 (1994), Liu, D. et al. J Biol Chem 279, 19239-46 (2004)). Signaling by both TNF-α and IFN-γ is required because animals deficient for TNF-α and IFN-γ receptors are refractory to the lethal effects of SEB and do not develop characteristic features of fulminant liver injury (Miethke et al. (1992), Pfeffer et al. (1993), Car et al. (1994)). This model depends also on MHC class II-expressing cells and CD4-positive lymphocytes because their deficiency renders mice refractory to SEB (Rajagopalan et al. *J Immunol* 169:1774-83 (2002), Yeung et al. *Eur J Immunol* 26:1074-82 (1996)). Consistent with these requirements, interference with the binding of SEB to its target on T cells protects D-galactosamine-sensitized mice from SEB lethality (Arad et al. *Nat Med* 6:414-21 (2000)). Thus, this in vivo model provides a well-defined and tractable system to analyze inflammatory cytokines-associated massive liver apoptosis that is relevant to human disease states based on systemic inflammation.

In systemic inflammation either the magnitude or duration of endogenous SOCS response was not sufficient to counteract the intracellular signaling in response to the bursts of inflammatory cytokines and chemokines triggered by SEB. Therefore the hypothesis that an in vivo balance in favor of pro-inflammatory intracellular transducers evoked by cytokines/chemokines unleashed by SEB can be shifted toward physiologic anti-inflammatory regulators by introduction of recombinant CP-SOCS3 was tested. To minimize the potential effect of low level of LPS detected in some recombinant SOCS3 preparations, C3H/HeJ mice were used in these in vivo experiments. These D-galactosamine-sensitized mice are hyporesponsive to the lethal effect of LPS but sensitive to the SEB toxicity (Yasuda et al. *J Endotoxin Res* 8:253-61 (2002)). Their sensitivity to SEB is comparable to that of widely used C57/BL6 mice (Liu et al. (2004)). In this in vivo setting intracellular protein therapy was examined with the CP-SOCS3 to enrich intracellular stores of SOCS3 as inflammation-suppressing measure. Consistent with the ex vivo demonstration of CP-SOCS3 inhibition of inflammatory cytokines, TNF-α and IL-6 in primary macrophages (FIG. 2F), suppression of IL-6 production by CP-SOCS3 in C3H/HeJ mice challenged with SEB and D-galactosamine (FIG. 4A) was observed. Administration of control HS3 protein (non-cell penetrating form of SOCS3) did not significantly suppress IL-6 production in vivo, consistent with its lack of an inhibitory effect in ex vivo-cultured cells (FIG. 2*f*). Thus, CP-SOCS3 suppresses the systemic inflammatory response to SEB as reflected by the inhibition of IL-6 expression.

Proinflammatory signaling exemplified by IFN-γ-evoked STAT1 phosphorylation leads to inducible expression of the MHC class II molecules that are required for SEB binding (Yeung et al. (1996), Arad et al. (2000). Therefore, the effect of recombinant SOCS3 proteins on inducible expression of MHC class II during SEB-triggered and T cell-mediated inflammatory response was analyzed. As documented in FIG. 4B, the treatment of mice with SEB and D-galactosamine increased the expression of MHC class II that reached peak at 48 h. This induction of MHC class II (calculated as 100%) was not significantly altered by a non-cell-penetrating HS3 protein (83%) administered intraperitoneally. In contrast, the induction of MHC class II was dramatically reduced to 14% and 10% following in vivo administration of CP-SOCS3 proteins HS3M and HMS3, respectively. This hitherto not reported effect of SOCS3 underscores its negative regulatory role in induction of MHC class II in vivo.

5. Example 5

Figure 4:
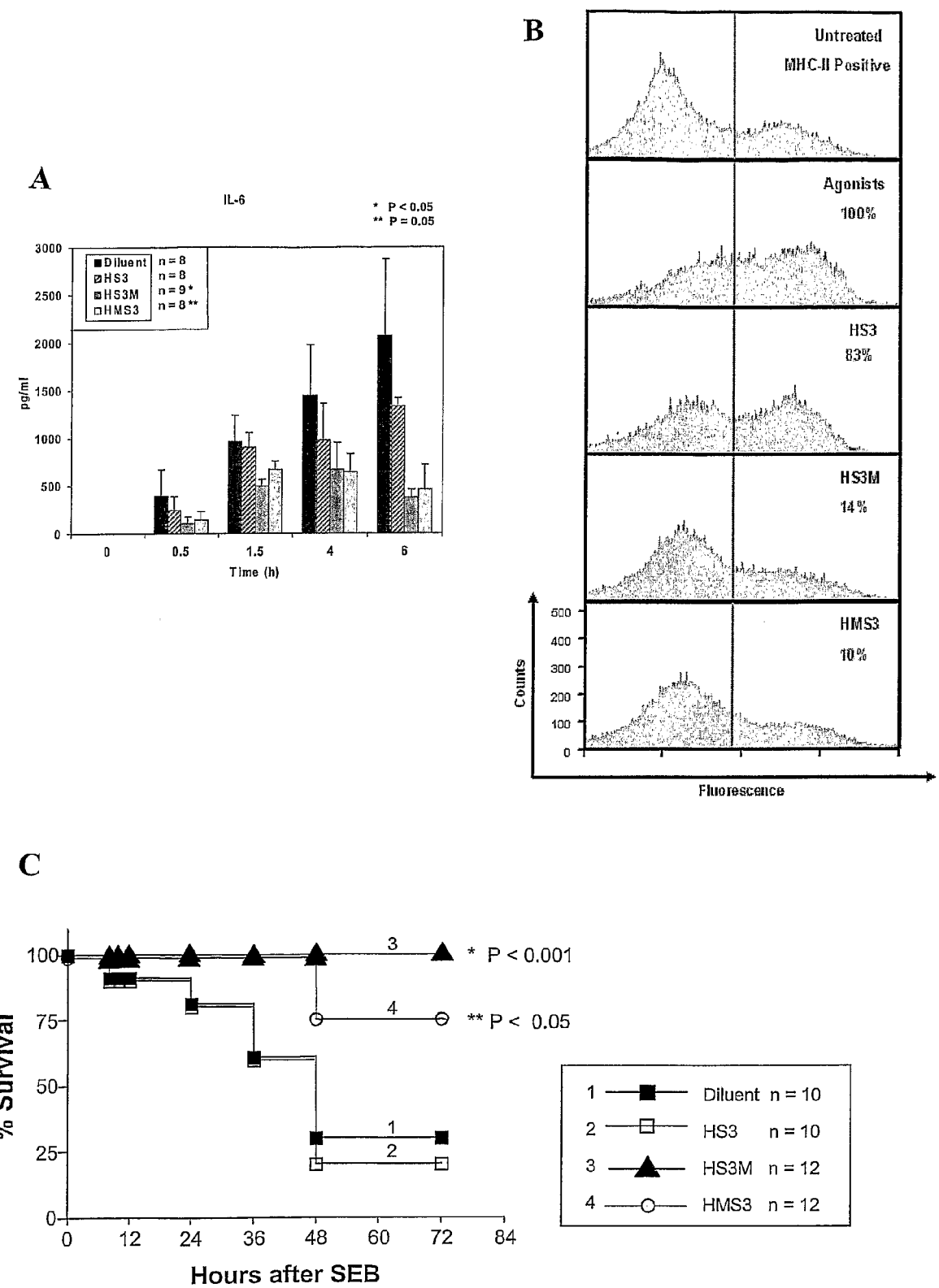
FIGS. 4A-4C show CP-SOCS3 proteins inhibit the production of inflammatory cytolcine IL-6 and the cell-surface expression of MHC class II in vivo and protect D-galactosamine-sensitized mice from SEB-induced death.

CP-SOCS3 Proteins Prevent Inflammation-Driven Liver Apoptosis and Death Caused by SEB The current paradigm of an acute systemic inflammatory response syndromes caused by SEB-like superantigens as well as other microbial agents portrays excessive bursts of inflammatory cytokines and chemokines as inciting vascular injury that underlies multiple organ failure leading to death (Cavaillon et al. *Scand J Infect Dis* 35:535-44 (2003)). Exogenous supply of recombinant CP-SOCS3 enriches intracellular stores of this inducible anti-inflammatory regulator and make mice more resistant to SEB. The in vivo effect of CP-SOCS3 forms was compared with non-CP-SOCS3 protein and diluent control on survival of mice challenged with SEB and D-galactosamine. As documented in FIG. 4C, 70 to 80% of C3H/HeJ mice treated with intraperitoneal injections of diluent or a control protein (HS3) showed progressive signs of sickness leading to death within 48 h after SEB/D-galactosamine challenge. In contrast, administration of HS3M produced a dramatically protective effect. All mice recovered fully from SEB/D-galactosamine challenge and survived at least 72 h. Thus, HS3M increased survival from 20% to 100%. Based on the log rank test, the difference in the survival rate between a CP-SOCS3-treated (HS3M) and control mice (diluent) was statistically significant ($p<0.001$). Mice that received another CP-SOCS3 protein (HMS3) were protected to the lesser degree (75% survival) albeit its death-sparing effect was also statistically significant ($p<0.05$) (FIG. 4C).

Figure 5:
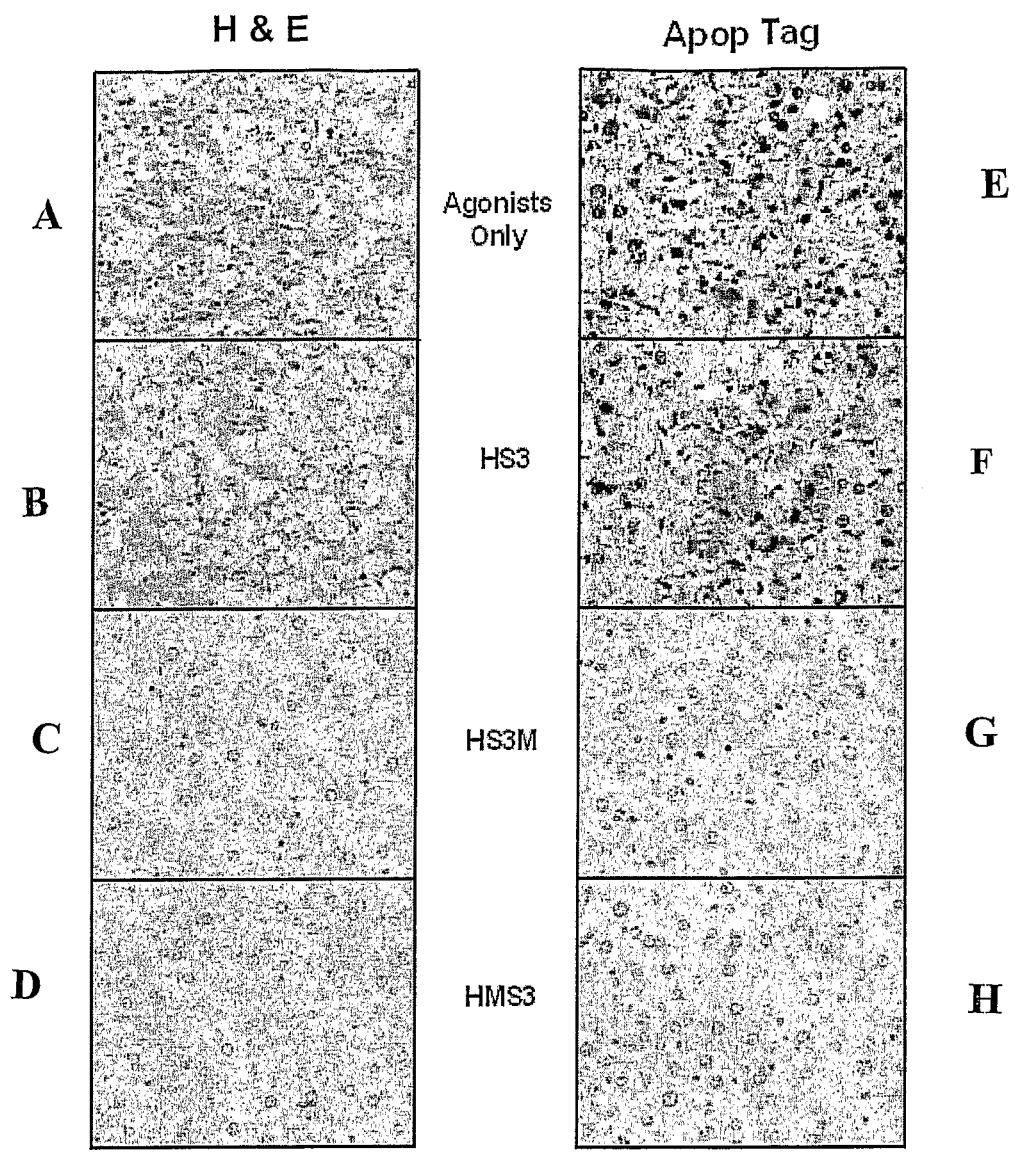
FIGS. 5A-5H show the prevention of SEB-induced liver apoptosis accompanied by hemorrhagicnecrosis in D-galactosamine-sensitized mice treated with CP-SOCS3 proteins. Histologic analysis of mice challenged with agonists (SEB/D-galactosamine) treated with diluent (FIGS. 5A, 5E), HS3 (FIGS. 5B, 5F), HS3M (FIG. 5C, 5G) or HMS3 (FIGS. 5D, 5H) was performed. Liver sections were stained with hematoxylin and eosin (H & E) (FIGS. 5A, 5B, 5C, 5D) or with Apop Tag (TUNEL assay) (FIGS. 5E, 5F, 5G, 5H). Note the hallmarks of acute liver injury (apoptosis, hepatocyte necrosis, and erythrocyte extravasation) in diluent and HS3 controls and preserved liver architecture without apoptosis and hemorrhagic necrosis in CP-SOCS3 (HS3M and HMS3)-treated mice.
Figure 6:
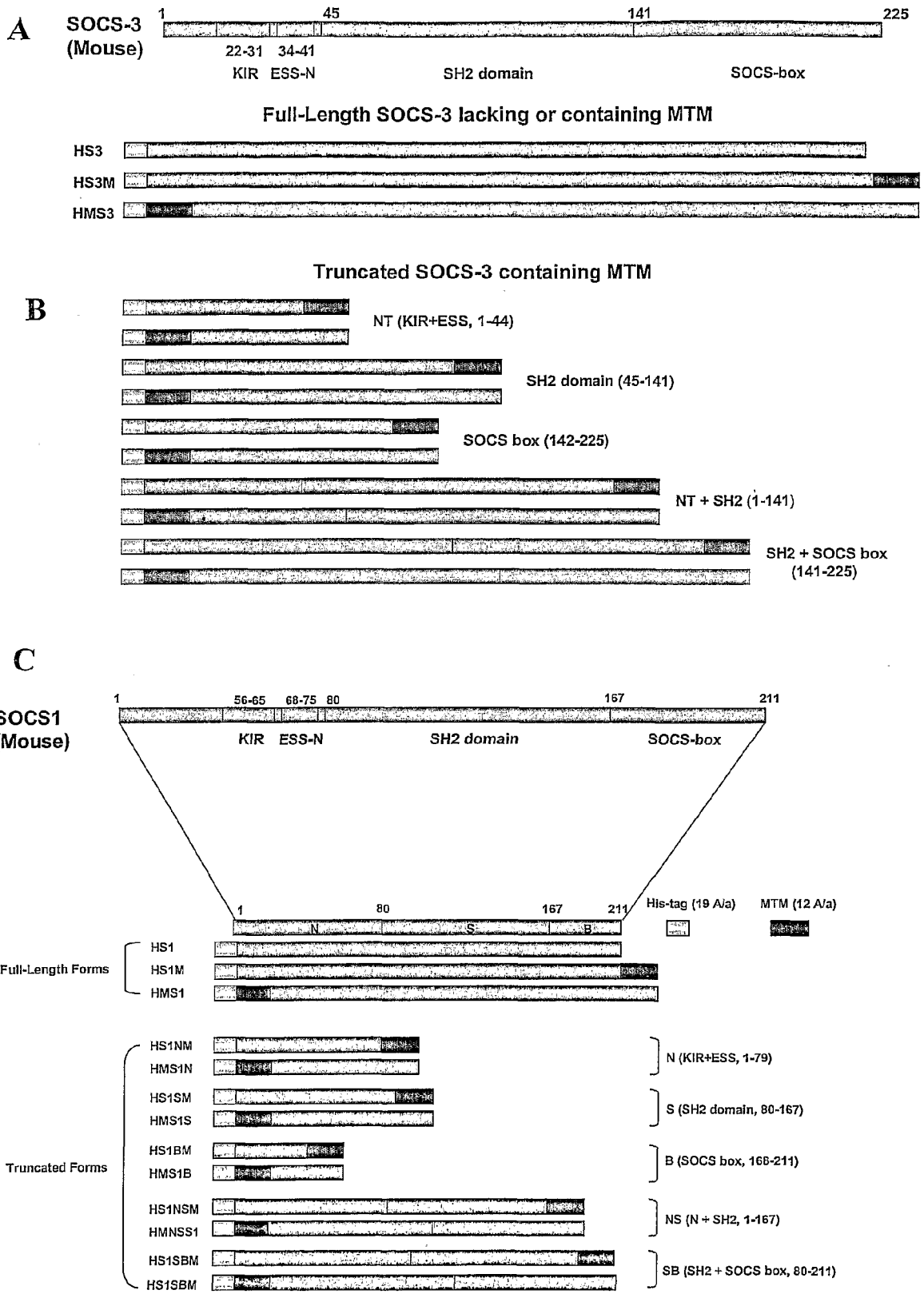
FIGS. 6A-6C show the structure and design of SOCS-1 and SOCS-3 and their fragments.

The survival of CP-SOCS3-treated mice was attributable to the cytoprotective effect in the liver, a primary target of inflammatory injury in D-galactosamine-sensitized mice (Miethke et al. (1992), Liu et al. (2004), Arad et al. (2000)). This was shown using histologic analysis of liver sections obtained from control mice challenged with SEB and treated with diluent or HS3, which showed diffuse hepatocellular injury marked by extensive apoptosis characterized by chromatin condensation and DNA fragmentation documented by TUNEL assay with Apop Tag reagent (FIG. 5E, F). In addition, hemorrhage and necrosis were prominent (FIG. 5A, B). In contrast, none of SEB-challenged mice that were treated with CP-SOSC3 (HS3M or HMS3) and survived for at least 72 h, displayed signs of hepatocellular liver injury. They had normal tissue architecture with no signs of apoptotic and/or necrotic liver injury compared to controls (diluent and HS3) (FIGS. 5C, D and 5G, H). Extended observation of these mice for 10 days demonstrated no signs of sickness or histologically-proven organ injury. Thus, it was concluded that the cytoprotective effect of CP-SOCS3 proteins correlated with the survival of mice challenged with SEB and D-galactosamine. Altogether, the anti-inflammatory and antiapoptotic effects of CP-SOCS3 proteins correlated with their death-sparing effect in this model of SEB-induced acute inflammation.

6. Example 6

General Methods

Design, expression, and purification of CP-SOCS3 proteins. Mouse SOCS3 cDNA (675 nt) was obtained (Starr et al. Nature 387, 917-21 (1997)). The MTM comprising a 12 amino acid sequence derived from FGF-4 and polyhistidine tag (His) were engineered as described before (Jo et al. *J Cell Biochem* 89:674-87 (2003), Jo et al. *Nat Biotechnol* 19: 929-33 (2001)). His-SOCS3 (HS3), His-SOCS3-MTM (HS3M) and His-MTM-SOCS3 (HMS3) were constructed by amplifying the SOCS3 cDNA from nt 1 to 678 using primer A and B for SOCS3 (225 amino acids), primer A and C for SOCS3-MTM (12 residues added to 225 amino acids of SOCS3) and primer D and B for MTM-SOCS3. The PCR products were subcloned into pGEM-T easy vector (Promega) and cleaved with Nde I. The amplified and cohesive-ended products were cloned into the Nde I site of the 6×His (SEQ ID NO: 30) expression vector, pET-28a (+) (Novagen). The resulting plasmids were used to express HS3, HS3M and HMS3 proteins under the control of the lacI promoter in *E. coli* strain BL21 (DE3) CodonPlus (Stratagen). The 6×His-tagged (SEQ ID NO: 30) recombinant proteins were purified by nickel-nitrilotriacetic acid (Ni-NTA) metal-affinity chromatography (as instructed by the supplier, Qiagen) under denaturing condition from *E. coli* BL21 cells grown to an A600 of 0.5-0.7 and induced for 2-3 hours with 0.7 mM isoprophyl-β-D-thiogalactoside (IPTG). Following affinity purification, HS3 was reconstituted in refolding buffer A (Tris 50 mM, NaCl 150 mM, L-arginine 0.88 M, reduced glutathione 1 mM, oxidized glutathione 1 mM, EDTA 1 mM, NDSB-201 100 mM, pH 8.0), and HS3M and HMS3 were reconstituted in refolding buffer B that was the same of buffer A except added guanidine HCl 0.55 M, and L-arginine 0.44 M. Reconstituted proteins were dialyzed for 6 h against cell culture medium (DMEM) containing 1% of penicillin-streptomycin and concentrated by ultrafiltration. Regardless of having a hydrophobic MTM or not, the purification process yielded soluble proteins at the concentration of >13 mg/L of bacteria culture, resulting in 30-45% of recovery from the purified proteins in denaturing condition (FIG. 1C). They contained 8-13 μg of LPS per mg of recombinant protein as determined by the Limulus chromogenic assay (Associates of Cape Cod). Prepared proteins were stored at −70° C. until use.

```
Primer A:
                                        (SEQ ID NO: 14)
CCGCATATGGTCACCCACAGCAAGTTTCCCGCC Primer B:
                                        (SEQ ID NO: 15)
CCGCATATGTTAAAGTGGAGCATCATACTGATC Primer C:
                                        (SEQ ID NO: 16)
CGCATATGTCAGGGTGCGGCAAGAAGAACAGGGAGAAGAACGGCTGCAAG
TGGAGCATCATACTGATC Primer D:
                                        (SEQ ID NO: 17)
CCGCATATGGCAGCCGTTCTTCTCCCTGTTCTTCTTGCCGCACCCGTCAC
CCACAGCAAGTTTCCCGCC
```

Protein Labeling and Intracellular Detection. Proteins were labeled with fluorescein isothiocyanate (FITC, Pierce Chemical) according to the manufacturer's instruction. After extensive dialysis (300 fold volume, 5 hours for each cycle repeated thrice) against DMEM to remove free FITC, labeled proteins were kept at −20° C. until use. FITC-labeled proteins were analyzed for their intracellular localization in RAW 264.7 (RAW) cells by confocal laser scanning microscopy using direct fluorescence. RAW cells were incubated with 1 μM FITC-labeled SOCS3 fusion proteins or free unconjugated FITC at room temperature for 10 minutes. To remove cell surface-attached proteins, the RAW cells were subsequently treated with proteinase K (5 μg/ml) for 10 min at 37° C. and washed three times with ice cold DMEM followed by a final addition of 0.2 ml of ice-cold phosphate-buffered saline, pH 7.4 (PBS). They were immediately observed without fixation using a fluorescence confocal laser-scanning microscope (Zeiss LSM510).

Phosphorylation of STAT1 Measured by Cytometric Beads Array and Immunoblotting. RAW cells were incubated with serum-free medium alone (DMEM), or with serum-free medium containing SOCS3 proteins of indicated concentrations for 1 h, followed by treatment with mouse recombinant IFN-γ (10 U/ml, Calbiochem) for 15 min. Phosphorylated STAT1 was measured in whole cell lysates by a cytometric bead array (CBA, BD Science, Pharmingen). Briefly, beads coated with capture antibody specific for phosphorylated (Tyr 701)-STAT1 were utilized. The p-STAT1 capture beads were mixed with the phycoerythrin (PE)-conjugated detection antibody specific for STAT1 and then incubated with recombinant standards or test samples to sandwich complexes. Following the acquisition of flow cytometric data, FACScalibur results were organized in graphical and tabular format using CBA analysis software (version 1.4, BD Sciences). Separately, whole cell lysates and cytosolic lysates were also prepared from RAW cells identically treated as described above except using mouse recombinant IFN-γ at 30 U/ml. Phosphorylation of STAT1 was detected by monoclonal anti-phospho Tyr 701 STAT1 antibody (Phosphorylated STAT1 CBA kit, BD Bioscience Pharmingen) and visualized by HRP-coupled goat anti-mouse IgG and chemiluminescence (ECL) western detection system (PerkinElmer Life Science). GAPDH was also visualized as internal loading control.

Cytokine/Chemokine Measurement. The TNF-α, IL-6 and MCP-1 concentration in the supernatants of cultured transformed (AMJ2-C8, ATCC) or primary macrophages were measured by a cytometric bead array (mouse inflammation CBA kit, BD Biosciences, Phanningen) according to the manufacturer's instructions. Briefly, beads coated with capture antibodies specific for an array of cytokines and chemokines were utilized. Cytokine capture beads were mixed with the PE-conjugated detection antibodies and then incubated with recombinant standards or test samples to sandwich complexes. AMJ2-C8 cells were pretreated with 10 μM SOCS3 proteins for 1 h and then stimulated with LPS (1 μg/ml) or/and IFN-γ (100 U/ml) for 4 h without the removal of SOCS3 proteins. Cell supernatants were collected for cytokine measurement after 4 h. Primary macrophages were obtained from peritoneal exudates produced in C3H/HeJ mice 24 h after intraperitoneal injection of 0.5 ml of 3% thioglycolate (Sigma). The mice were euthanized, and the peritoneal cavity was washed with PBS. Isolated cells were pretreated with 10 μM SOCS3 proteins for 1 h and stimulated with LPS (1 μg/ml) or/and IFN-γ (100 U/ml) in presence of SOCS3 proteins for 24 h. Supernatants were collected after 24 h for measurement of TNF-α and IL-6. Following the acquisition of flow cytometric data, FACScalibur results were organized in graphical and tabular format using CBA analysis software.

Detection of CP-SOCS3 Proteins in Blood and Spleen Cells. FITC-labeled SOCS3 proteins were tracked in blood cells and in spleen cells of C3H/HeJ mice using FACS analysis. Briefly, whole blood was collected from the periorbital plexus into heparin-containing tubes at indicated time after intraperitoneal injection of FITC-SOCS3 proteins (70 μg in 0.7 ml) or equimolar concentration of FITC. White blood cell-rich fraction was prepared by differential centrifugation followed by the lysis of residual erythrocytes and analyzed by FACS. The mice were immediately sacrificed after blood collection and their spleens were excised, rinsed in PBS, gently homogenized between two microscopic slides. The erythrocytes were removed by brief hypotonic lysis. The washed splenocytes were suspended in PBS. The blood leukocytes and lymphocytes, and total splenocytes were incubated with proteinase K (5 μg/ml) for 10 min at 37° C. prior to FACS analysis to degrade any cell-surface bound FITC-SOCS3 proteins. FACS analysis (FACScalibur; Becton and Dickinson, San Jose, Calif.) was done using a forward versus side light scatter, and green fluorescence was collected with a 530±30-nanometer band pass filter.

In Vivo Model of SEB-induced Inflammation and Liver Apoptosis. C3H/HeJ male mice purchased from the Jackson laboratory were 8-10 weeks with an average weight of 20 grams. Mice were sensitized by intraperitoneal injection of D-galactosamine (20 mg/200 µl/mouse, Sigma) 30 min before they were challenged with intraperitoneal (ip) injection of SEB (280 µg/300 µl/mouse, Toxin Technology). SOCS3 proteins (0.3 µg/µl, 300 µl/injection/mouse) or diluent (DMEM) were injected intraperitoneally into mice before (30 min) and after (30 min, 1.5 h, 2.5 h, 4.5 h and 6.5 h) SEB challenge. Animals were observed at hourly intervals for signs of systemic toxicity (pilorection, ataxia, and the lack of reaction to cage motion). Surviving mice were euthanized at 72 h. Animal handling and experimental procedures were performed in accordance with the American Association of Accreditation of Laboratory Animal Care guidelines and approved by the Institutional Animal Care and Use Committee.

In Vivo IL-6 Assay in Blood. C3H/HeJ mice received an ip injection of SEB and D-galactosamine as described above. SOCS3 proteins were also injected intraperitoneally as described above. Blood samples (50 µl) taken from the saphenous vein were collected in heparinized tubes before (30 min) and after SEB challenge at indicated intervals (0.5, 1.5, 4 and 6 h) shown. A plasma level of IL-6 was measured by a cytometric bead array according to the manufacturer's instructions.

Measurement of MHC Class II Expression In Vivo. To determine the level of MHC class II molecules in monocytes and macrophages, total splenocytes were isolated from mice that were untreated or treated with diluent or SOCS3 proteins and sacrificed 48 h after SEB/D-galactosamine challenge. Cells were preincubated with anti-mouse Fc antibody (dilution 1:40, Pharmingen) for 30 min and probed with PE-conjugated anti-mouse I-Ak (A$\alpha$k) antibody (dilution 1:100, Pharmingen) plus FITC-conjugated anti-mouse Mac-1 (CD11b) antibody (dilution 1:100, Pharmingen) for 15 min. The doubly positive (Mac-1 and I-Ak) cells were analyzed in FACScalibur. The value of 100% represents the increment in the number of double positive (CD11b & I-Ak) cells between untreated and agonist only-treated mice. The inhibition of MHC-II in CD 11b-positive cells treated with SOCS3 protein represents the % of double positive cells as compared to the 100% in agonist only-treated mice.

Histologic Analysis. Tissue samples (liver, spleen, kidney, lung and heart) were collected from the mice that were observed for signs of systemic toxicity during the course of the experiment and euthanized. Formalin-fixed and paraffin-embedded sections were stained with hematoxylin and eosin. Apoptosis of liver cells was evaluated by histology and by TUNEL (TdT-dependent dUTP-biotin nick end labeling) assay using the Apop Tag reagent (Chemicon) according to the manufacturer's instructions.

Statistical Analysis. All experimental data obtained from cultured macrophages were expressed as mean±S.D. A student's t test was used to determine the significance of the difference. A two way repeated measure analysis of variance (RM ANOVA) and a log rank test were used to determine the significance of the difference in in vivo cytokine production and survival, respectively.

G. References

1. Hawiger, J. Innate immunity and inflammation: a transcriptional paradigm. Immunol Res 23, 99-109 (2001).
2. Alexander, W. S. Suppressors of cytokine signalling (SOCS) in the immune system. Nat Rev Immunol 2, 410-6 (2002).
3. Krebs, D. L. & Hilton, D. J. SOCS: physiological suppressors of cytokine signaling. J Cell Sci 113 (Pt 16), 2813-9 (2000).
4. Krebs, D. L. & Hilton, D. J. SOCS proteins: negative regulators of cytokine signaling. Stem Cells 19, 378-87 (2001).
5. Yasukawa, H., Sasaki, A. & Yoshimura, A. Negative regulation of cytokine signaling pathways. Annu Rev Immunol 18, 143-64 (2000).
6. Zhang, J. G. et al. The SOCS box of suppressor of cytokine signaling-1 is important for inhibition of cytokine action in vivo. Proc Natl Acad Sci USA 98, 13261-5 (2001).
7. Yasukawa, H. et al. IL-6 induces an anti-inflammatory response in the absence of SOCS3 in macrophages. Nat Immunol 4, 551-6 (2003).
8. Lang, R. et al. SOCS3 regulates the plasticity of gp130 signaling. Nat Immunol 4, 546-50 (2003).
9. Croker, B. A. et al. SOCS3 negatively regulates IL-6 signaling in vivo. Nat Immunol 4, 540-5 (2003).
10. Balaban, N. & Rasooly, A. Analytical chromatography for recovery of small amounts of staphylococcal enterotoxins from food. Int J Food Microbiol 64, 33-40 (2001).
11. Dinges, M. M., Orwin, P. M. & Schlievert, P. M. Exotoxins of *Staphylococcus aureus*. Clin Microbiol Rev 13, 16-34, table of contents (2000).
12. Mattix, M. E., Hunt, R. E., Wilhelmsen, C. L., Johnson, A. J. & Baze, W. B. Aerosolized staphylococcal enterotoxin B-induced pulmonary lesions in rhesus monkeys (Macaca mulatta). Toxicol Pathol 23, 262-8 (1995).
13. Madsen, J. M. Toxins as weapons of mass destruction. A comparison and contrast with biological-warfare and chemical-warfare agents. Clin Lab Med 21, 593-605 (2001).
14. Fey, P. D. et al. Comparative molecular analysis of community- or hospital-acquired methicillin-resistant *Staphylococcus aureus*. Antimicrob Agents Chemother 47, 196-203 (2003).
15. Clark, N. M., Hershberger, E., Zervosc, M. J. & Lynch, J. P., 3rd. Antimicrobial resistance among gram-positive organisms in the intensive care unit. Curr Opin Crit Care 9, 403-12, (2003).
16. Miethke, T. et al. T cell-mediated lethal shock triggered in mice by the superantigen staphylococcal enterotoxin B: critical role of tumor necrosis factor. J Exp Med 175, 91-8 (1992).
17. Pfeffer, K. et al. Mice deficient for the 55 kd tumor necrosis factor receptor are resistant to endotoxic shock, yet succumb to *L. monocytogenes* infection. Cell 73, 457-67 (1993).
18. Car, B. D. et al. Interferon gamma receptor deficient mice are resistant to endotoxic shock. J Exp Med 179, 1437-44 (1994).
19. Hawiger, J. Noninvasive intracellular delivery of functional peptides and proteins. Curr Opin Chem Biol 3, 89-94 (1999).
20. Lee, J. Y. & Sullivan, K. E. Gamma interferon and lipopolysaccharide interact at the level of transcription to induce tumor necrosis factor alpha expression. Infect Immun 69, 2847-52 (2001).
21. Poltorak, A. et al. Defective LPS signaling in C3H/HeJ and C57BL/10ScCr mice: mutations in Tlr4 gene. Science 282, 2085-8 (1998).
22. Stoiber, D. et al. Lipopolysaccharide induces in macrophages the synthesis of the suppressor of cytokine signaling 3 and suppresses signal transduction in response to the activating factor IFN-gamma. J Immunol 163, 2640-7 (1999).
23. Hoebe, K. et al. Identification of Lps2 as a key transducer of MyD88-independent TIR signalling. Nature 424, 743-8 (2003).

24. Fitzgerald, K. A. et al. LPS-TLR4 signaling to IRF-3/7 and NF-kappaB involves the toll adapters TRAM and TRIF. J Exp Med 198, 1043-55 (2003).
25. Oshiumi, H. et al. TIR-containing adapter molecule (TICAM)-2, a bridging adapter recruiting to toll-like receptor 4 TICAM-1 that induces interferon-beta. J Biol Chem 278, 49751-62 (2003).
26. Liu, D. et al. Suppression of Staphylococcal Enterotoxin B-induced Toxicity by a Nuclear Import Inhibitor. J Biol Chem 279, 19239-46 (2004).,
27. Rajagopalan, G., Smart, M. K., Krco, C. J. & David, C. S. Expression and function of transgenic HLA-DQ molecules and lymphocyte development in mice lacking invariant chain. J Immunol 169, 1774-83 (2002).
28. Yeung, R. S. et al. Human CD4 and human major histocompatibility complex class II (DQ6) transgenic mice: supersensitivity to superantigen-induced septic shock. Eur J Imnunol 26, 1074-82 (1996).
29. Arad, G., Levy, R., Hillman, D. & Kaempfer, R. Superantigen antagonist protects against lethal shock and defines a new domain for T-cell activation. Nat Med 6, 414-21 (2000).
30. Yasuda, S., Nagaki, M. & Moriwaki, H. Staphylococcal enterotoxin B induces hepatic injury and lethal shock in endotoxin-resistant C3H/HeJ mice despite a deficient macrophage response. J Endotoxin Res 8, 253-61 (2002).
31. Cavaillon, J. M., Adib-Conquy, M., Fitting, C., Adrie, C. & Payen, D. Cytokine cascade in sepsis. Scand J Infect Dis 35, 535-44 (2003).
32. Rui, L., Yuan, M., Frantz, D., Shoelson, S. & White, M. F. SOCS-1 and SOCS-3 block insulin signaling by ubiquitin-mediated degradation of IRS1 and IRS2. J Biol Chem 277, 42394-8 (2002).
33. Veach, R. A. et al. Receptor/transporter-independent targeting of functional peptides across the plasma membrane. J Biol Chem 279, 11425-31 (2004).
34. Hawiger, J. Cellular import of functional peptides to block intracellular signaling. Curr Opin Ihmunol 9, 189-94 (1997).
35. O'Keefe, G. M., Nguyen, V. T., Ping Tang, L. L. & Benveniste, E. N. IFN-gamma regulation of class II transactivator promoter IV in macrophages and microglia: involvement of the suppressors of cytokine signaling-1 protein. J Immunol 166, 2260-9 (2001).
36. Shouda, T. et al. Induction of the cytokine signal regulator SOCS3/CIS3 as a therapeutic strategy for treating inflammatory arthritis. J Clin Invest 108, 1781-8 (2001).
37. Suzuki, A. et al. CIS3/SOCS3/SSI3 plays a negative regulatory role in STAT3 activation and intestinal inflammation. J Exp Med 193, 471-81 (2001).
38. Starr, R. et al. A family of cytokine-inducible inhibitors of signalling. Nature 387, 917-21 (1997).
39. Jo, D. et al. Cell cycle-dependent transduction of cell-penetrating Cre recombinase proteins. J Cell Biochem 89, 674-87 (2003).
40. Jo, D. et al. Epigenetic regulation of gene structure and function with a cell-permeable Cre recombinase. Nat Biotechnol 19, 929-33 (2001).

What is claimed is:

1. A method of treating inflammation in a subject suffering from inflammation comprising: administering a soluble isolated polypeptide comprising a suppressor of cytokine signaling 1 or 3 (SOCS1; SOCS3) sequence and a membrane translocating sequence at either an amino or carboxy terminal end of the SOCS sequence to the subject,
   wherein the inflammation is associated with a viral or bacterial infection.

2. The method of claim 1, wherein the severity of the inflammation of the subject is reduced.

3. The method of claim 1, wherein the infection is a viral infection.

4. The method of claim 1, wherein the infection is a bacterial infection.

5. The method of claim 4, wherein the bacterial infection is a *Staphylococcus aureus* infection.

6. The method of claim 1, wherein the soluble isolated polypeptide is encoded by an isolated nucleic acid comprising the human SOCS3 nucleotide sequence set forth in SEQ ID NO: 11.

7. The method of claim 1, wherein the soluble isolated polypeptide is encoded by an isolated nucleic acid comprising the human SOCS1 nucleotide sequence set forth in SEQ ID NO: 18.

8. The method of claim 1, wherein the soluble isolated polypeptide further comprises a purification sequence.

9. The method of claim 8, wherein the purification sequence is a polyhistidine tag.

10. The method of claim 1, wherein the soluble isolated polypeptide is administered with a pharmaceutically acceptable carrier, diluent or excipient in a pharmaceutical composition.

11. A method of treating inflammation in a subject suffering from inflammation comprising: administering a soluble isolated polypeptide comprising a suppressor of cytokine signaling 1 or 3 (SOCS1; SOCS3) sequence and a membrane translocating sequence at either an amino or carboxy terminal end of the SOCS sequence to the subject,
wherein the inflammation is associated with a viral or bacterial infection, and wherein the soluble isolated polypeptide is administered to the subject at a time point selected from the group consisting of: prior to surgery, and after surgery.

12. The method of claim 11, wherein the soluble isolated polypeptide is administered to the subject after surgery.

13. The method of claim 11, wherein the soluble isolated polypeptide is encoded by an isolated nucleic acid comprising the human SOCS3 nucleotide sequence set forth in SEQ ID NO: 11.

14. The method of claim 11, wherein the soluble isolated polypeptide is encoded by an isolated nucleic acid comprising the human SOCS1 nucleotide sequence set forth in SEQ ID NO: 18.

15. The method of claim 11, wherein the soluble isolated polypeptide further comprises a purification sequence.

16. The method of claim 15, wherein the purification sequence is a polyhistidine tag.

17. The method of claim 11, wherein the soluble isolated polypeptide is administered with a pharmaceutically acceptable carrier, diluent or excipient in a pharmaceutical composition.

18. A method of treating a *Staphylococcus aureus* infection in a subject suffering from a *Staphylococcus aureus* infection comprising: administering a soluble isolated polypeptide comprising a suppressor of cytokine signaling 1 or 3 (SOCS1; SOCS3) sequence and a membrane translocating sequence at either an amino or carboxy terminal end of the SOCS sequence to the subject.

19. The method of claim 18, wherein the soluble isolated polypeptide is encoded by an isolated nucleic acid comprising the human SOCS3 nucleotide sequence set forth in SEQ ID NO: 11.

20. The method of claim 18, wherein the soluble isolated polypeptide is encoded by an isolated nucleic acid comprising the human SOCS1 nucleotide sequence set forth in SEQ ID NO: 18.

21. The method of claim 18, wherein the soluble isolated polypeptide is administered with a pharmaceutically acceptable carrier, diluent or excipient in a pharmaceutical composition.

* * * * *

SEQUENCE LISTING

```
<160> NUMBER OF SEQ ID NOS: 30

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Gly Ser Ser His His His His His His Ser Ser Leu Val Pro Arg
1               5                   10                  15

Gly Ser His

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ala Val Leu Leu Pro Val Leu Leu Ala Ala Pro
1               5                   10

<210> SEQ ID NO 3
<211> LENGTH: 211
<212> TYPE: PRT
<213> ORGANISM: Homo sapiens
```

```
<400> SEQUENCE: 3

Met Val Ala His Asn Gln Val Ala Asp Asn Ala Val Ser Thr Ala
1               5                   10                  15

Ala Glu Pro Arg Arg Pro Glu Pro Ser Ser Ser Ser Ser Ser Ser
            20                  25                  30

Pro Ala Ala Pro Ala Arg Pro Arg Pro Cys Pro Ala Val Pro Ala Pro
                35                  40                  45

Ala Pro Gly Asp Thr His Phe Arg Thr Phe Arg Ser His Ala Asp Tyr
    50                  55                  60

Arg Arg Ile Thr Arg Ala Ser Leu Leu Asp Ala Cys Gly Phe Tyr
65                  70                  75                  80

Trp Gly Pro Leu Ser Val His Gly Ala His Glu Arg Leu Arg Ala Glu
                85                  90                  95

Pro Val Gly Thr Phe Leu Val Arg Asp Ser Arg Gln Arg Asn Cys Phe
                100                 105                 110

Phe Ala Leu Ser Val Lys Met Ala Ser Gly Pro Thr Ser Ile Arg Val
            115                 120                 125

His Phe Gln Ala Gly Arg Phe His Leu Asp Gly Ser Arg Glu Ser Phe
130                 135                 140

Asp Cys Leu Phe Glu Leu Leu Glu His Tyr Val Ala Ala Pro Arg Arg
145                 150                 155                 160

Met Leu Gly Ala Pro Leu Arg Gln Arg Arg Val Arg Pro Leu Gln Glu
                165                 170                 175

Leu Cys Arg Gln Arg Ile Val Ala Thr Val Gly Arg Glu Asn Leu Ala
            180                 185                 190

Arg Ile Pro Leu Asn Pro Val Leu Arg Asp Tyr Leu Ser Ser Phe Pro
            195                 200                 205

Phe Gln Ile
    210

<210> SEQ ID NO 4
<211> LENGTH: 225
<212> TYPE: PRT
<213> ORGANISM: Homo sapiens

<400> SEQUENCE: 4

Met Val Thr His Ser Lys Phe Pro Ala Ala Gly Met Ser Arg Pro Leu
1               5                   10                  15

Asp Thr Ser Leu Arg Leu Lys Thr Phe Ser Ser Lys Ser Glu Tyr Gln
            20                  25                  30

Leu Val Val Asn Ala Val Arg Lys Leu Gln Glu Ser Gly Phe Tyr Trp
            35                  40                  45

Ser Ala Val Thr Gly Gly Glu Ala Asn Leu Leu Leu Ser Ala Glu Pro
    50                  55                  60

Ala Gly Thr Phe Leu Ile Arg Asp Ser Ser Asp Gln Arg His Phe Phe
65                  70                  75                  80

Thr Leu Ser Val Lys Thr Gln Ser Gly Thr Lys Asn Leu Arg Ile Gln
                85                  90                  95

Cys Glu Gly Gly Ser Phe Ser Leu Gln Ser Asp Pro Arg Ser Thr Gln
                100                 105                 110

Pro Val Pro Arg Phe Asp Cys Val Leu Lys Leu Val His His Tyr Met
            115                 120                 125

Pro Pro Pro Gly Ala Pro Ser Phe Pro Ser Pro Pro Thr Glu Pro Ser
130                 135                 140
```

```
Ser Glu Val Pro Glu Gln Pro Ser Ala Gln Pro Leu Pro Gly Ser Pro
145                 150                 155                 160

Pro Arg Arg Ala Tyr Tyr Ile Tyr Ser Gly Gly Glu Lys Ile Pro Leu
                165                 170                 175

Val Leu Ser Arg Pro Leu Ser Ser Asn Val Ala Thr Leu Gln His Leu
            180                 185                 190

Cys Arg Lys Thr Val Asn Gly His Leu Asp Ser Tyr Glu Lys Val Thr
        195                 200                 205

Gln Leu Pro Gly Pro Ile Arg Glu Phe Leu Asp Gln Tyr Asp Ala Pro
    210                 215                 220

Leu
225

<210> SEQ ID NO 5
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Gly Ser Ser His His His His His His Ser Ser Gly Leu Val Pro
1               5                   10                  15

Arg Gly Ser Met Val Ala Arg Asn Gln Val Ala Ala Asp Asn Ala Ile
            20                  25                  30

Ser Pro Ala Ala Glu Pro Arg Arg Ser Glu Pro Ser Ser Ser Ser
        35                  40                  45

Ser Ser Ser Ser Pro Ala Ala Pro Val Arg Pro Arg Pro Cys Pro Ala
50                  55                  60

Val Pro Ala Pro Ala Pro Gly Asp Thr His Phe Arg Thr Phe Arg Ser
65                  70                  75                  80

His Ser Asp Tyr Arg Arg Ile Thr Arg Thr Ser Ala Leu Leu Asp Ala
                85                  90                  95

Cys Gly Phe Tyr Trp Gly Pro Leu Ser Val His Gly Ala His Glu Arg
            100                 105                 110

Leu Arg Ala Glu Pro Val Gly Thr Phe Leu Val Arg Asp Ser Arg Gln
        115                 120                 125

Arg Asn Cys Phe Phe Ala Leu Ser Val Lys Met Ala Ser Gly Pro Thr
130                 135                 140

Ser Ile Arg Val His Phe Gln Ala Gly Arg Phe His Leu Asp Gly Ser
145                 150                 155                 160

Arg Glu Thr Phe Asp Cys Leu Phe Glu Leu Leu Glu His Tyr Val Ala
                165                 170                 175

Ala Pro Arg Arg Met Leu Gly Ala Pro Leu Arg Gln Arg Arg Val Arg
            180                 185                 190

Pro Leu Gln Glu Leu Cys Arg Gln Arg Ile Val Ala Ala Val Gly Arg
        195                 200                 205

Glu Asn Leu Ala Arg Ile Pro Leu Asn Pro Val Leu Arg Asp Tyr Leu
    210                 215                 220

Ser Ser Phe Pro Phe Gln Ile Ala Ala Val Leu Leu Pro Val Leu Leu
225                 230                 235                 240

Ala Ala Pro

<210> SEQ ID NO 6
<211> LENGTH: 243
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 6

```
Met Gly Ser Ser His His His His His His Ser Ser Gly Leu Val Pro
1               5                   10                  15

Arg Gly Ser Ala Ala Val Leu Leu Pro Val Leu Leu Ala Ala Pro Met
            20                  25                  30

Val Ala Arg Asn Gln Val Ala Ala Asp Asn Ala Ile Ser Pro Ala Ala
        35                  40                  45

Glu Pro Arg Arg Arg Ser Glu Pro Ser Ser Ser Ser Ser Ser Ser Ser
50                  55                  60

Pro Ala Ala Pro Val Arg Pro Arg Pro Cys Pro Ala Val Pro Ala Pro
65                  70                  75                  80

Ala Pro Gly Asp Thr His Phe Arg Thr Phe Arg Ser His Ser Asp Tyr
                85                  90                  95

Arg Arg Ile Thr Arg Thr Ser Ala Leu Leu Asp Ala Cys Gly Phe Tyr
            100                 105                 110

Trp Gly Pro Leu Ser Val His Gly Ala His Glu Arg Leu Arg Ala Glu
        115                 120                 125

Pro Val Gly Thr Phe Leu Val Arg Asp Ser Arg Gln Arg Asn Cys Phe
130                 135                 140

Phe Ala Leu Ser Val Lys Met Ala Ser Gly Pro Thr Ser Ile Arg Val
145                 150                 155                 160

His Phe Gln Ala Gly Arg Phe His Leu Asp Gly Ser Arg Glu Thr Phe
                165                 170                 175

Asp Cys Leu Phe Glu Leu Leu Glu His Tyr Val Ala Ala Pro Arg Arg
            180                 185                 190

Met Leu Gly Ala Pro Leu Arg Gln Arg Arg Val Arg Pro Leu Gln Glu
        195                 200                 205

Leu Cys Arg Gln Arg Ile Val Ala Ala Val Gly Arg Glu Asn Leu Ala
210                 215                 220

Arg Ile Pro Leu Asn Pro Val Leu Arg Asp Tyr Leu Ser Ser Phe Pro
225                 230                 235                 240

Phe Gln Ile
```

<210> SEQ ID NO 7
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

```
Met Gly Ser Ser His His His His His His Ser Ser Gly Leu Val Pro
1               5                   10                  15

Arg Gly Ser Met Val Thr His Ser Lys Phe Pro Ala Ala Gly Met Ser
            20                  25                  30

Arg Pro Leu Asp Thr Ser Leu Arg Leu Lys Thr Phe Ser Ser Lys Ser
        35                  40                  45

Glu Tyr Gln Leu Val Val Asn Ala Val Arg Lys Leu Gln Glu Ser Gly
50                  55                  60

Phe Tyr Trp Ser Ala Val Thr Gly Gly Glu Ala Asn Leu Leu Leu Ser
65                  70                  75                  80
```

```
Ala Glu Pro Ala Gly Thr Phe Leu Ile Arg Asp Ser Ser Asp Gln Arg
                85                  90                  95

His Phe Phe Thr Leu Ser Val Lys Thr Gln Ser Gly Thr Lys Asn Leu
            100                 105                 110

Arg Ile Gln Cys Glu Gly Gly Ser Phe Ser Leu Gln Ser Asp Pro Arg
        115                 120                 125

Ser Thr Gln Pro Val Pro Arg Phe Asp Cys Val Leu Lys Leu Val His
    130                 135                 140

His Tyr Met Pro Pro Pro Gly Thr Pro Ser Phe Ser Leu Pro Pro Thr
145                 150                 155                 160

Glu Pro Ser Ser Glu Val Pro Glu Gln Pro Ala Gln Ala Leu Pro
                165                 170                 175

Gly Ser Thr Pro Lys Arg Ala Tyr Tyr Ile Tyr Ser Gly Gly Glu Lys
                180                 185                 190

Ile Pro Leu Val Leu Ser Arg Pro Leu Ser Ser Asn Val Ala Thr Leu
            195                 200                 205

Gln His Leu Cys Arg Lys Thr Val Asn Gly His Leu Asp Ser Tyr Glu
        210                 215                 220

Lys Val Thr Gln Leu Pro Gly Pro Ile Arg Glu Phe Leu Asp Gln Tyr
225                 230                 235                 240

Asp Ala Pro Leu

<210> SEQ ID NO 8
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Gly Ser Ser His His His His His His Ser Ser Gly Leu Val Pro
1               5                   10                  15

Arg Gly Ser Met Val Thr His Ser Lys Phe Pro Ala Ala Gly Met Ser
            20                  25                  30

Arg Pro Leu Asp Thr Ser Leu Arg Leu Lys Thr Phe Ser Ser Lys Ser
        35                  40                  45

Glu Tyr Gln Leu Val Val Asn Ala Val Arg Lys Leu Gln Glu Ser Gly
    50                  55                  60

Phe Tyr Trp Ser Ala Val Thr Gly Gly Glu Ala Asn Leu Leu Leu Ser
65                  70                  75                  80

Ala Glu Pro Ala Gly Thr Phe Leu Ile Arg Asp Ser Ser Asp Gln Arg
                85                  90                  95

His Phe Phe Thr Leu Ser Val Lys Thr Gln Ser Gly Thr Lys Asn Leu
            100                 105                 110

Arg Ile Gln Cys Glu Gly Gly Ser Phe Ser Leu Gln Ser Asp Pro Arg
        115                 120                 125

Ser Thr Gln Pro Val Pro Arg Phe Asp Cys Val Leu Lys Leu Val His
    130                 135                 140

His Tyr Met Pro Pro Pro Gly Thr Pro Ser Phe Ser Leu Pro Pro Thr
145                 150                 155                 160

Glu Pro Ser Ser Glu Val Pro Glu Gln Pro Ala Gln Ala Leu Pro
                165                 170                 175

Gly Ser Thr Pro Lys Arg Ala Tyr Tyr Ile Tyr Ser Gly Gly Glu Lys
                180                 185                 190

Ile Pro Leu Val Leu Ser Arg Pro Leu Ser Ser Asn Val Ala Thr Leu
```

```
                195                 200                 205
Gln His Leu Cys Arg Lys Thr Val Asn Gly His Leu Asp Ser Tyr Glu
        210                 215                 220

Lys Val Thr Gln Leu Pro Gly Pro Ile Arg Glu Phe Leu Asp Gln Tyr
225                 230                 235                 240

Asp Ala Pro Leu Ala Ala Val Leu Leu Pro Val Leu Leu Ala Ala Pro
                245                 250                 255

<210> SEQ ID NO 9
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Gly Ser Ser His His His His His His Ser Ser Gly Leu Val Pro
1               5                   10                  15

Arg Gly Ser Ala Ala Val Leu Leu Pro Val Leu Leu Ala Ala Pro Met
            20                  25                  30

Val Thr His Ser Lys Phe Pro Ala Ala Gly Met Ser Arg Pro Leu Asp
        35                  40                  45

Thr Ser Leu Arg Leu Lys Thr Phe Ser Ser Lys Ser Glu Tyr Gln Leu
    50                  55                  60

Val Val Asn Ala Val Arg Lys Leu Gln Glu Ser Gly Phe Tyr Trp Ser
65                  70                  75                  80

Ala Val Thr Gly Gly Glu Ala Asn Leu Leu Leu Ser Ala Glu Pro Ala
                85                  90                  95

Gly Thr Phe Leu Ile Arg Asp Ser Ser Asp Gln Arg His Phe Phe Thr
            100                 105                 110

Leu Ser Val Lys Thr Gln Ser Gly Thr Lys Asn Leu Arg Ile Gln Cys
        115                 120                 125

Glu Gly Gly Ser Phe Ser Leu Gln Ser Asp Pro Arg Ser Thr Gln Pro
    130                 135                 140

Val Pro Arg Phe Asp Cys Val Leu Lys Leu Val His His Tyr Met Pro
145                 150                 155                 160

Pro Pro Gly Thr Pro Ser Phe Ser Leu Pro Thr Glu Pro Ser Ser
                165                 170                 175

Glu Val Pro Glu Gln Pro Pro Ala Gln Ala Leu Pro Gly Ser Thr Pro
            180                 185                 190

Lys Arg Ala Tyr Tyr Ile Tyr Ser Gly Gly Glu Lys Ile Pro Leu Val
        195                 200                 205

Leu Ser Arg Pro Leu Ser Ser Asn Val Ala Thr Leu Gln His Leu Cys
    210                 215                 220

Arg Lys Thr Val Asn Gly His Leu Asp Ser Tyr Glu Lys Val Thr Gln
225                 230                 235                 240

Leu Pro Gly Pro Ile Arg Glu Phe Leu Asp Gln Tyr Asp Ala Pro Leu
                245                 250                 255

<210> SEQ ID NO 10
<211> LENGTH: 1121
<212> TYPE: DNA
<213> ORGANISM: Mus musculus

<400> SEQUENCE: 10
gcgatctgtg ggtgacagtg tctgcgagag actttgccac accattctgc cggaatttgg    60
```

-continued

| | | |
|---|---|---|
| agaaaaagaa ccagccgctt ccagtcccct ccccctccgc caccatttcg acaccctgc | 120 | |
| acactctcgt tttggggtac cctgtgactt ccaggcagca cgcgaggtcc actggcccca | 180 | |
| gctcgggcga ccagctgtct gggacgtgtt gactcatctc ccatgaccct gcggtgcctg | 240 | |
| gagccctccg ggaatggagc ggacaggacg cggagccagt gggggaccgc ggggttgccg | 300 | |
| gaggaacagt cccccgaggc ggcgcgtctg gcgaaagccc tgcgcgagct cagtcaaaca | 360 | |
| ggatggtact ggggaagtat gactgttaat gaagccaaag agaaattaaa agaggctcca | 420 | |
| gaaggaactt tcttgattag agatagttcg cattcagact acctactaac tatatccgtt | 480 | |
| aagacgtcag ctggaccgac taacctgcgg attgagtacc aagatgggaa attcagattg | 540 | |
| gattctatca tatgtgtcaa gtccaagctt aaacagtttg acagtgtggt tcatctgatt | 600 | |
| gactactatg tccagatgtg caaggataaa cggacaggcc cagaagcccc acggaatggg | 660 | |
| actgttcacc tgtacctgac caaacctctg tatacatcag cacccactct gcagcatttc | 720 | |
| tgtcgactcg ccattaacaa atgtaccggt acgatctggg gactgccttt accaacaaga | 780 | |
| ctaaaagatt acttggaaga atataaattc caggtataag tatttctctc tcttttttcgt | 840 | |
| ttttttttaa aaaaaaaaa acacatgcct catatagact atctccgaat gcagctatgt | 900 | |
| gaaagagaac ccagaggccc tcctctggat aactgcgcag aattctctct taaggacagt | 960 | |
| tgggctcagt ctaacttaaa ggtgtgaaga tgtagctagg tattttaaag ttcccctag | 1020 | |
| gtagttttag ctgaatgatg cttctctttcc tatggctgct caagatcaaa tggcccttt | 1080 | |
| aaatgaaaca aacaaaaca aacaaaaaa aaaaaaaaa a | 1121 | |

<210> SEQ ID NO 11
<211> LENGTH: 2746
<212> TYPE: DNA
<213> ORGANISM: Homo sapiens

<400> SEQUENCE: 11

| | | |
|---|---|---|
| ggctccgact tggactccct gctccgctgc tgccgcttcg gccccgcacg cagccagccg | 60 | |
| ccagccgccc gccggcccca gctcccgccg cggccccttg ccgcggtccc tctcctggtc | 120 | |
| ccctcccggt tggtccgggg gtgcgcaggg ggcagggcgg gcgcccaggg gaagctcgag | 180 | |
| ggacgcgcgc gcgaaggctc ctttgtggac ttcacggccg ccaacatctg ggcgcagcgc | 240 | |
| gggccaccgc tggccgtctc gccgccgcgt cgccttgggg acccgagggg gctcagcccc | 300 | |
| aaggacggag acttcgattc gggaccagcc ccccgggatg cggtagcggc cgctgtgcgg | 360 | |
| aggccgcgaa gcagctgcag ccgccgccgc gcagatccac gctggctccg tgcgccatgg | 420 | |
| tcacccacag caagtttccc gccgcggga tgagccgccc cctggacacc agcctgcgcc | 480 | |
| tcaagaccctt cagctccaag agcgagtacc agctggtggt gaacgcagtg cgcaagctgc | 540 | |
| aggagagcgg cttctactgg agcgcagtga ccggcggcga ggcgaacctg ctgctcagtg | 600 | |
| ccgagcccgc cggcaccttt ctgatccgcg acagctcgga ccagcgccac ttcttcacgc | 660 | |
| tcagcgtcaa gacccagtct gggaccaaga acctgcgcat ccagtgtgag ggggcagct | 720 | |
| tctctctgca gagcgatccc cggagcacgc agcccgtgcc ccgcttcgac tgcgtgctca | 780 | |
| agctggtgca ccactacatg ccgccccctg agccccctc cttcccctcg ccacctactg | 840 | |
| aacccctcctc cgaggtgccc gagcagccgt ctgcccagcc actccctggg agtcccccca | 900 | |
| gaagagccta ttacatctac tccgggggcg agaagatccc cctggtgttg agccggcccc | 960 | |
| tctcctccaa cgtggccact cttcagcatc tctgtcggaa gaccgtcaac ggccacctgg | 1020 | |
| actcctatga gaaagtcacc cagctgccgg ggcccattcg ggagttcctg gaccagtacg | 1080 | |

-continued

```
atgccccgct ttaaggggta aagggcgcaa agggcatggg tcgggagagg ggacgcaggc      1140
ccctctcctc cgtggcacat ggcacaagca caagaagcca accaggagag agtcctgtag      1200
ctctgggggg aaagagggcg acaggccccc tccctctgcc ctctccctgc agaatgtggc      1260
aggcggacct ggaatgtgtt ggagggaagg gggagtacca cctgagtctc cagcttctcc      1320
ggaggagcca gctgtcctgg tgggacgata gcaaccacaa gtggattctc cttcaattcc      1380
tcagcttccc ctctgcctcc aaacagggga cacttcggga atgctgaact aatgagaact      1440
gccagggaat cttcaaactt tccaacggaa cttgtttgct ctttgatttg gtttaaacct      1500
gagctggttg tggagcctgg gaaggtggaa agagagagag gtcctgaggg ccccagggct      1560
gcgggctggc gaaggaaatg gtcacacccc ccgcccaccc caggcgagga tcctggtgac      1620
atgctcctct ccctggctcc ggggagaagg gcttggggtg acctgaaggg aaccatcctg      1680
gtaccccaca tcctctcctc cgggacagtc accgaaaaca caggttccaa agtctacctg      1740
gtgcctgaga gcccagggcc cttcctccgt tttaaggggg aagcaacatt tggaggggat      1800
ggatgggctg gtcagctggt ctccttttcc tactcatact ataccttcct gtacctgggt      1860
ggatggagcg ggaggatgga ggagacggga catctttcac ctcaggctcc tggtagagaa      1920
gacaggggat tctactctgt gcctcctgac tatgtctggc taagagattc gccttaaatg      1980
ctccctgtcc catggagagg gacccagcat aggaaagcca catactcagc tggatgggt      2040 ggagaggctg agggactcac tggagggcac caagccagcc acagccagg gaagtgggga      2100 gggggggcgg aaacccatgc ctcccagctg agcactggga atgtcagccc agtaagtatt      2160
ggccagtcag gcgcctcgtg gtcagagcag agccaccagg tcccactgcc ccgagccctg      2220
cacagccctc cctcctgcct gggtggggga ggctggaggt cattggagag ctggactgc      2280 tgccaccccg ggtgctcccg ctctgccata gcactgatca gtgacaattt acaggaatgt      2340
agcagcgatg gaattacctg gaacagtttt ttgtttttgt ttttgttttt gttttgtgg      2400 ggggggcaa ctaaacaaac acaaagtatt ctgtgtcagg tattggctg acagggcag       2460 ttgtgtgttg gggtggtttt tttctctatt tttttgtttg tttcttgttt tttaataatg      2520
tttacaatct gcctcaatca ctctgtcttt tataaagatt ccacctccag tcctctctcc      2580
tcccccctac tcaggccctt gaggctatta ggagatgctt gaagaactca acaaaatccc      2640
aatccaagtc aaactttgca catatttata tttatattca gaaaagaaac atttcagtaa      2700
tttataataa agagcactat ttttttaatga aaaaaaaaa aaaaaa                    2746
```

<210> SEQ ID NO 12
<211> LENGTH: 198
<212> TYPE: PRT
<213> ORGANISM: Mus musculus

<400> SEQUENCE: 12

```
Met Thr Leu Arg Cys Leu Glu Pro Ser Gly Asn Gly Ala Asp Arg Thr
1               5                   10                  15

Arg Ser Gln Trp Gly Thr Ala Gly Leu Pro Glu Glu Gln Ser Pro Glu
            20                  25                  30

Ala Ala Arg Leu Ala Lys Ala Leu Arg Glu Leu Ser Gln Thr Gly Trp
        35                  40                  45

Tyr Trp Gly Ser Met Thr Val Asn Glu Ala Lys Glu Lys Leu Lys Glu
    50                  55                  60

Ala Pro Glu Gly Thr Phe Leu Ile Arg Asp Ser Ser His Ser Asp Tyr
65                  70                  75                  80

Leu Leu Thr Ile Ser Val Lys Thr Ser Ala Gly Pro Thr Asn Leu Arg
```

```
                    85                  90                  95
Ile Glu Tyr Gln Asp Gly Lys Phe Arg Leu Asp Ser Ile Ile Cys Val
            100                 105                 110
Lys Ser Lys Leu Lys Gln Phe Asp Ser Val Val His Leu Ile Asp Tyr
            115                 120                 125
Tyr Val Gln Met Cys Lys Asp Lys Arg Thr Gly Pro Glu Ala Pro Arg
            130                 135                 140
Asn Gly Thr Val His Leu Tyr Leu Thr Lys Pro Leu Tyr Thr Ser Ala
145                 150                 155                 160
Pro Thr Leu Gln His Phe Cys Arg Leu Ala Ile Asn Lys Cys Thr Gly
                165                 170                 175
Thr Ile Trp Gly Leu Pro Leu Pro Thr Arg Leu Lys Asp Tyr Leu Glu
            180                 185                 190
Glu Tyr Lys Phe Gln Val
            195

<210> SEQ ID NO 13
<211> LENGTH: 2545
<212> TYPE: DNA
<213> ORGANISM: Mus musculus

<400> SEQUENCE: 13
```

| | | | | |
|---|---|---|---|---|
| ctcgcctgct cttacgaccg ctgtctctcc gggctcccgg acgccccctt cccggcccag | 60 |
| ctctccgtcg aggtccctcg cccaggtcct ttgcctgatt cgcccaggag tgcgcctcat | 120 |
| cggcccgggg agcagcgaag ccagagggg cgcacgcacg gggagcccct ttgtagactt | 180 |
| cacggctgcc aacatctggg cgcagcgcga gccactgctg gccgccgcct cgcctcgggg | 240 |
| accataggag gcgcagcccc aaggccggag atttcgcttc gggactagct ccccgggatg | 300 |
| cggtagcggc cgctgtgcgg aggccgcgaa gcagctgcag ccaccgccgc gcagatccac | 360 |
| gctggctccg tgcgccatgg tcacccacag caagtttccc gccgccggga tgagccgccc | 420 |
| cctggacacc agcctgcgcc tcaagacctt cagctccaaa agcgagtacc agctggtggt | 480 |
| gaacgccgtg cgcaagctgc aggagagcgg attctactgg agcgccgtga ccggcggcga | 540 |
| ggcgaacctg ctgctcagcg ccgagcccgc gggcaccttt cttatccgcg acagctcgga | 600 |
| ccagcgccac ttcttcacgt tgagcgtcaa gacccagtcg ggaccaagaa acctacgcat | 660 |
| ccagtgtgag gggggcagct tttcgctgca gagtgaccc cgaagcacgc agccagttcc | 720 |
| ccgcttcgac tgtgtactca agctggtgca ccactacatg ccgcctccag ggaccccctc | 780 |
| cttttctttg ccacccacgg aaccctcgtc cgaagttccg gagcagccac ctgcccaggc | 840 |
| actccccggg agtaccccca agagagctta ctacatctat tctgggggcg agaagattcc | 900 |
| gctggtactg agccgacctc tctcctccaa cgtggccacc tccagcatc tttgtcggaa | 960 |
| gactgtcaac ggccacctgg actcctatga gaaagtgacc cagctgcctg gacccattcg | 1020 |
| ggagttcctg gatcagtatg atgctccact ttaaggagca aaagggtcag agggggggcct | 1080 |
| gggtcggtcg gtcgcctctc ctccgaggca catggcacaa gcacaaaaat ccagccccaa | 1140 |
| cggtcggtag ctcccagtga gccaggggca gattggcttc ttcctcaggc cctccactcc | 1200 |
| cgcagagtag agctggcagg acctggaatt cgtctgaggg gagggggagc tgccacctgc | 1260 |
| tttcccccct ccccccagctc cagcttcttt caagtggagc cagccggcct ggcctggtgg | 1320 |
| gacaataccat ttgacaagcg gactctcccc tccccttcct ccacaccccc tctgcttccc | 1380 |
| aagggaggtg gggacacctc caagtgttga acttagaact gcaaggggaa tcttcaaact | 1440 |
| ttcccgctgg aacttgtttg cgctttgatt tggtttgatc aagagcaggc acctggggga | 1500 |

```
aggatggaag agaaaagggt gtgtgaaggg tttttatgct ggccaaagaa ataaccactc    1560
ccactgccca acctaggtga ggagtggtgg ctcctggctc tggggagagt ggcaaggggt    1620
gacctgaaga gagctatact ggtgccaggc tcctctccat ggggcagcta atgaaacctc    1680
gcagatccct tgcacccag aaccctcccc gttgtgaaga ggcagtagca tttagaaggg     1740
agacagatga ggctggtgag ctggccgcct tttccaacac cgaagggagg cagatcaaca    1800
gatgagccat cttggagccc aggtttccct ggagcagatg gagggttctg ctttgtctct    1860
cctatgtggg gctaggagac tcgccttaaa tgccctctgt cccagggatg gggattggca    1920
cacaaggagc caaacacagc caataggcag agagttgagg gattcaccca ggtggctaca    1980
ggccagggga gtggctgca ggggagagac ccagtcactc aggagactcc tgagttaaca     2040
ctgggaagac attggccagt cctagtcatc tctcggtcag taggtccgag agcctccagg    2100
ccctgcacag ccctcccttc tcacctgggg ggaggcagga ggtgatggag aagccttccc    2160
atgccgctca caggggcctc acgggaatgc agcagccatg caattacctg gaactggtcc    2220
tgtgttgggg agaaacaagt tttctgaagt caggtatggg gctgggtggg gcagctgtgt    2280
gttggggtgg ctttttctc tctgttttga ataatgttta caatttgcct caatcactt      2340 tataaaaatc cacctccagc ccgcccctct ccccactcag gccttcgagg ctgtctgaag    2400
atgcttgaaa aactcaacca aatcccagtt caactcagac tttgcacata tatttatatt    2460
tatactcaga aagaaacat ttcagtaatt tataataaaa gagcactatt ttttaatgaa     2520
aaaaaaaaaa aaaaaaaaaa aaaaa                                          2545

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccgcatatgg tcacccacag caagtttccc gcc                                  33

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccgcatatgt taaagtggag catcatactg atc                                  33

<210> SEQ ID NO 16
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgcatatgtc agggtgcggc aagaagaaca gggagaagaa cggctgcaag tggagcatca    60
tactgatc                                                              68

<210> SEQ ID NO 17
```

```
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccgcatatgg cagccgttct tctccctgtt cttcttgccg cacccgtcac ccacagcaag    60
tttcccgcc                                                           69

<210> SEQ ID NO 18
<211> LENGTH: 1216
<212> TYPE: DNA
<213> ORGANISM: Homo sapiens

<400> SEQUENCE: 18
ggcagctgca cggctcctgg ccccggagca tgcgcgagag ccgccccgga gcgcccggga     60 gcccccgcc gtcccgcccg cggcgtcccg cgccccgccg ccagcgcacc cccggacgct    120
atggcccacc cctccggctg gccccttctg taggatggta gcacacaacc aggtggcagc   180
cgacaatgca gtccacacag cagcagagcc ccgacggcgg ccagaacctt cctcctcttc   240
ctcctcctcg cccgcggccc ccgcgcgccc gcggccgtgc cccgcggtcc cggccccggc   300
ccccggcgac acgcacttcc gcacattccg ttcgcacgcc gattaccggc gcatcacgcg   360
cgccagcgcg ctcctggacg cctgcggatt ctactggggg ccctgagcg tgcacggggc   420 gcacgagcgg ctgcgcgccg agcccgtggg caccttcctg gtgcgcgaca gccgccagcg   480
gaactgcttt ttcgccctta gcgtgaagat ggcctcggga cccacgagca tccgcgtgca   540
ctttcaggcc ggccgctttc acctggatgg cagccgcgag agcttcgact gcctcttcga   600
gctgctggag cactacgtgg cggcgccgcg ccgcatgctg ggggccccgc tgcgccagcg   660
ccgcgtgcgg ccgctgcagg agctgtgccg ccagcgcatc gtggccaccg tgggccgcga   720
gaacctggct cgcatccccc tcaaccccgt cctccgcgac tacctgagct ccttcccctt   780
ccagatttga ccggcagcgc ccgccgtgca cgcagcatta actgggatgc cgtgttattt   840
tgttattact tgcctggaac catgtgggta ccctccccgg cctggggttgg agggagcgga   900 tgggtgtagg ggcgaggcgc ctcccgcccct cggctggaga cgaggccgca gaccccttct   960
cacctcttga gggggtcctc cccctcctgg tgctccctct gggtccccct ggttgttgta  1020
gcagcttaac tgtatctgga gccaggacct gaactcgcac ctcctacctc ttcatgttta  1080 catatacccca gtatctttgc acaaaccagg ggttggggga gggtctctgg ctttatttt   1140 ctgctgtgca gaatcctatt ttatattttt taaagtcagt ttaggtaata aactttatta  1200
tgaaagtttt tttttt                                                  1216

<210> SEQ ID NO 19
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Gly Ser Ser His His His His His His Ser Ser Gly Leu Val Pro
1               5                   10                  15

Arg Gly Ser Met Val Thr His Ser Lys Phe Pro Ala Ala Gly Met Ser
            20                  25                  30
```

```
Arg Pro Leu Asp Thr Ser Leu Arg Leu Lys Thr Phe Ser Ser Lys Ser
            35                  40                  45

Glu Tyr Gln Leu Val Val Asn Ala Val Arg Lys Leu Gln Glu Ser Gly
 50                  55                  60

Phe Tyr Trp Ser Ala Val Thr Gly Gly Glu Ala Asn Leu Leu Leu Ser
 65                  70                  75                  80

Ala Glu Pro Ala Gly Thr Phe Leu Ile Arg Asp Ser Ser Asp Gln Arg
                    85                  90                  95

His Phe Phe Thr Leu Ser Val Lys Thr Gln Ser Gly Thr Lys Asn Leu
            100                 105                 110

Arg Ile Gln Cys Glu Gly Gly Ser Phe Ser Leu Gln Ser Asp Pro Arg
            115                 120                 125

Ser Thr Gln Pro Val Pro Arg Phe Asp Cys Val Leu Lys Leu Val His
130                 135                 140

His Tyr Met Pro Pro Pro Gly Thr Pro Ser Phe Ser Leu Pro Pro Thr
145                 150                 155                 160

Glu Pro Ser Ser Glu Val Pro Glu Gln Pro Pro Ala Gln Ala Leu Pro
                    165                 170                 175

Gly Ser Thr Pro Lys Arg Ala Tyr Tyr Ile Tyr Ser Gly Gly Glu Lys
                    180                 185                 190

Ile Pro Leu Val Leu Ser Arg Pro Leu Ser Ser Asn Val Ala Thr Leu
                    195                 200                 205

Gln His Leu Cys Arg Lys Thr Val Asn Gly His Leu Asp Ser Tyr Glu
            210                 215                 220

Lys Val Thr Gln Leu Pro Gly Pro Ile Arg Glu Phe Leu Asp Gln Tyr
225                 230                 235                 240

Asp Ala Pro Leu Ala Ala Val Leu Leu Pro Val Leu Leu Ala Ala Pro
                    245                 250                 255

<210> SEQ ID NO 20
<211> LENGTH: 198
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Thr Leu Arg Cys Leu Glu Pro Ser Gly Asn Gly Gly Glu Gly Thr
 1               5                  10                  15

Arg Ser Gln Trp Gly Thr Ala Gly Ser Ala Glu Glu Pro Ser Pro Gln
                20                  25                  30

Ala Ala Arg Leu Ala Lys Ala Leu Arg Glu Leu Gly Gln Thr Gly Trp
            35                  40                  45

Tyr Trp Gly Ser Met Thr Val Asn Glu Ala Lys Glu Lys Leu Lys Glu
 50                  55                  60

Ala Pro Glu Gly Thr Phe Leu Ile Arg Asp Ser Ser His Ser Asp Tyr
 65                  70                  75                  80

Leu Leu Thr Ile Ser Val Lys Thr Ser Ala Gly Pro Thr Asn Leu Arg
                    85                  90                  95

Ile Glu Tyr Gln Asp Gly Lys Phe Arg Leu Asp Ser Ile Ile Cys Val
                    100                 105                 110

Lys Ser Lys Leu Lys Gln Phe Asp Ser Val Val His Leu Ile Asp Tyr
            115                 120                 125

Tyr Val Gln Met Cys Lys Asp Lys Arg Thr Gly Pro Glu Ala Pro Arg
130                 135                 140
```

Asn Gly Thr Val His Leu Tyr Leu Thr Lys Pro Leu Tyr Thr Ser Ala
145                 150                 155                 160

Pro Ser Leu Gln His Leu Cys Arg Leu Thr Ile Asn Lys Cys Thr Gly
            165                 170                 175

Ala Ile Trp Gly Leu Pro Leu Pro Thr Arg Leu Lys Asp Tyr Leu Glu
            180                 185                 190

Glu Tyr Lys Phe Gln Val
            195

<210> SEQ ID NO 21
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gly Ser Ser His His His His His His Ser Ser Gly Leu Val Pro
1               5                   10                  15

Arg Gly Ser Ala Ala Val Leu Leu Pro Val Leu Leu Ala Ala Pro Met
            20                  25                  30

Val Thr His Ser Lys Phe Pro Ala Ala Gly Met Ser Arg Pro Leu Asp
        35                  40                  45

Thr Ser Leu Arg Leu Lys Thr Phe Ser Ser Lys Ser Glu Tyr Gln Leu
    50                  55                  60

Val Val Asn Ala Val Arg Lys Leu Gln Glu Ser Gly Phe Tyr Trp Ser
65                  70                  75                  80

Ala Val Thr Gly Gly Glu Ala Asn Leu Leu Leu Ser Ala Glu Pro Ala
                85                  90                  95

Gly Thr Phe Leu Ile Arg Asp Ser Ser Asp Gln Arg His Phe Phe Thr
            100                 105                 110

Leu Ser Val Lys Thr Gln Ser Gly Thr Lys Asn Leu Arg Ile Gln Cys
        115                 120                 125

Glu Gly Gly Ser Phe Ser Leu Gln Ser Asp Pro Arg Ser Thr Gln Pro
    130                 135                 140

Val Pro Arg Phe Asp Cys Val Leu Lys Leu Val His His Tyr Met Pro
145                 150                 155                 160

Pro Pro Gly Thr Pro Ser Phe Ser Leu Pro Pro Thr Glu Pro Ser Ser
            165                 170                 175

Glu Val Pro Glu Gln Pro Pro Ala Gln Ala Leu Pro Gly Ser Thr Pro
            180                 185                 190

Lys Arg Ala Tyr Tyr Ile Tyr Ser Gly Gly Glu Lys Ile Pro Leu Val
        195                 200                 205

Leu Ser Arg Pro Leu Ser Ser Asn Val Ala Thr Leu Gln His Leu Cys
    210                 215                 220

Arg Lys Thr Val Asn Gly His Leu Asp Ser Tyr Glu Lys Val Thr Gln
225                 230                 235                 240

Leu Pro Gly Pro Ile Arg Glu Phe Leu Asp Gln Tyr Asp Ala Pro Leu
            245                 250                 255

<210> SEQ ID NO 22
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Met Gly Ser Ser His His His His His Ser Gly Leu Val Pro
1               5                   10                  15

Arg Gly Ser Met Val Thr His Ser Lys Phe Pro Ala Ala Gly Met Ser
            20                  25                  30

Arg Pro Leu Asp Thr Ser Leu Arg Leu Lys Thr Phe Ser Ser Lys Ser
        35                  40                  45

Glu Tyr Gln Leu Val Val Asn Ala Val Arg Lys Leu Gln Glu Ser Gly
    50                  55                  60

Phe Tyr Trp Ser Ala Val Thr Gly Gly Glu Ala Asn Leu Leu Leu Ser
65                  70                  75                  80

Ala Glu Pro Ala Gly Thr Phe Leu Ile Arg Asp Ser Ser Asp Gln Arg
                85                  90                  95

His Phe Phe Thr Leu Ser Val Lys Thr Gln Ser Gly Thr Lys Asn Leu
            100                 105                 110

Arg Ile Gln Cys Glu Gly Gly Ser Phe Ser Leu Gln Ser Asp Pro Arg
        115                 120                 125

Ser Thr Gln Pro Val Pro Arg Phe Asp Cys Val Leu Lys Leu Val His
    130                 135                 140

His Tyr Met Pro Pro Pro Gly Thr Pro Ser Phe Ser Leu Pro Pro Thr
145                 150                 155                 160

Glu Pro Ser Ser Glu Val Pro Glu Gln Pro Ala Gln Ala Leu Pro
                165                 170                 175

Gly Ser Thr Pro Lys Arg Ala Tyr Tyr Ile Tyr Ser Gly Gly Glu Lys
            180                 185                 190

Ile Pro Leu Val Leu Ser Arg Pro Leu Ser Ser Asn Val Ala Thr Leu
        195                 200                 205

Gln His Leu Cys Arg Lys Thr Val Asn Gly His Leu Asp Ser Tyr Glu
    210                 215                 220

Lys Val Thr Gln Leu Pro Gly Pro Ile Arg Glu Phe Leu Asp Gln Tyr
225                 230                 235                 240

Asp Ala Pro Leu
```

<210> SEQ ID NO 23
<211> LENGTH: 2210
<212> TYPE: DNA
<213> ORGANISM: Homo sapiens

<400> SEQUENCE: 23

| | |
|---|---|
| agccgcggcc tcaactaaaa gtggccattg acctttcaag ctttcgagca gtgatgcaat | 60 |
| agaatagtat ttcaaagaaa aatgcttatc gaaattttgg atccggtttt cccgtgattg | 120 |
| ttaagggttt cttttaaaaa gtaggtcaca tttcaagtag gtcatatttc ggggcgggt | 180 |
| gcgcagacaa ggagatgagt ttccactaag gccaggggc ctccaacggg gttggaggtg | 240 |
| agaatcccag gtagggtaga ggtgccgaga tccttccgaa tcccagccct ggggcgtcag | 300 |
| ccctgcaggg aatggcagag acactctccg gactgaggga accgaggcca gtcaccaagc | 360 |
| cccttccggg cgcgcaggcg atcagtgggt gaccgcggct gcgagggact ttgtcatccg | 420 |
| tcctccagga tctggggaga aagagccccca tcccttctct ctctgccacc atttcggaca | 480 |
| ccccgcaggg actcgttttg ggattcgcac tgacttcaag gaaggacgcg aacccttctc | 540 |
| tgacccccagc tcgggcggcc acctgtcttt gccgcggtga cccttctctc atgaccctgc | 600 |
| ggtgccttga gccctccggg aatggcgggg aaggacgcg agccagtgg gggaccgcgg | 660 |
| ggtcggcgga ggagccatcc ccgcaggcgg cgcgtctggc gaaggccctg cgggagctcg | 720 |

```
gtcagacagg atggtactgg ggaagtatga ctgttaatga agccaaagag aaattaaaag    780
aggcaccaga aggaactttc ttgattagag atagctcgca ttcagactac ctactaacaa    840
tatctgttaa acatcagct ggaccaacta atcttcgaat cgaataccaa gacggaaaat    900
tcagattgga ctctatcata tgtgtcaaat ccaagcttaa acaatttgac agtgtggttc    960
atctgatcga ctactatgtt cagatgtgca aggataagcg gacaggtcca gaagccccc    1020
ggaacggcac tgttcacctt tatctgacca aaccgctcta cacgtcagca ccatctctgc    1080
agcatctctg taggctcacc attaacaaat gtaccggtgc catctgggga ctgcctttac    1140
caacaagact aaaagattac ttggaagaat ataaattcca ggtataaatg tttctctttt    1200
tttaaacatg tctcacatag agtatctccg aatgcagcta tgtaaaagag aaccaaaact    1260
tgagtgctct ggataactat atggaatgct ttctaagaac agctgaagct aatctaattt    1320
aaatttaaca gcttgaagag gtagctaggt gtttaaagtt cctccagata cttttacctg    1380
agtgatgctt cccttcctaa ggctgaccaa gacctgttga tccttttaga ttaaaaataa    1440
aatgtcgcat gtaaaggctg aagtcgcgtt ttatcagaat gccttgcctt cttaggttct    1500
tttccattat gtcaaaggtc caggctccag taggagagaa agaactcctc ataggaatac    1560
tgaagaagtg ggaaggaacc aagctgacac aggcctcact gcaatttgat atgcctgctg    1620
atcagagtct cttgggcatt ttatattttg cattctgatg tacctaggag ttttgttaaa    1680
cagatgatgt atgtgagtat ttatcccatt ttatgcaatt aaccaaatca accaaaaaaa    1740
gtgaccatga agtcctgtat ttgtcttttt actacatgta ggaactctca tgtgaatgag    1800
tactgtagta atccattcta tgggagcctt atttcagaaa tatttcaaac tggtgcaaat    1860
ggaaaagact ttctctttc ctttaaagct aaagacaaga atatcatgct atacaggtgc    1920
aactcaatcc ccgttaataa aaaccaatgt aggtataggc attctaccct ttgaaatagc    1980
tgtgtcccaa cctgttgcca ttgatttttt ggaaatggct ttagaaatat ccaagttgtc    2040
cttgaattgt ctaaccatgg acataaacag ttgtctccct tctactgtgt agaatacttt    2100
gacttaattt tcttccagat acaggggggat acctgcctgt ttttcaaagt gtttatttac    2160
tgctgttact atttgattag aatgtattaa ataaaaaaaa cctgatttct                2210
```

<210> SEQ ID NO 24
<211> LENGTH: 225
<212> TYPE: PRT
<213> ORGANISM: Mus musculus

<400> SEQUENCE: 24

```
Met Val Thr His Ser Lys Phe Pro Ala Ala Gly Met Ser Arg Pro Leu
1               5                   10                  15

Asp Thr Ser Leu Arg Leu Lys Thr Phe Ser Ser Lys Ser Glu Tyr Gln
            20                  25                  30

Leu Val Val Asn Ala Val Arg Lys Leu Gln Glu Ser Gly Phe Tyr Trp
        35                  40                  45

Ser Ala Val Thr Gly Gly Glu Ala Asn Leu Leu Leu Ser Ala Glu Pro
    50                  55                  60

Ala Gly Thr Phe Leu Ile Arg Asp Ser Ser Asp Gln Arg His Phe Phe
65                  70                  75                  80

Thr Leu Ser Val Lys Thr Gln Ser Gly Thr Lys Asn Leu Arg Ile Gln
                85                  90                  95

Cys Glu Gly Gly Ser Phe Ser Leu Gln Ser Asp Pro Arg Ser Thr Gln
            100                 105                 110
```

```
Pro Val Pro Arg Phe Asp Cys Val Leu Lys Leu Val His His Tyr Met
        115                 120                 125

Pro Pro Pro Gly Thr Pro Ser Phe Ser Leu Pro Thr Glu Pro Ser
        130                 135                 140

Ser Glu Val Pro Glu Gln Pro Ala Gln Ala Leu Pro Gly Ser Thr
145                 150                 155                 160

Pro Lys Arg Ala Tyr Tyr Ile Tyr Ser Gly Gly Glu Lys Ile Pro Leu
                165                 170                 175

Val Leu Ser Arg Pro Leu Ser Ser Asn Val Ala Thr Leu Gln His Leu
                180                 185                 190

Cys Arg Lys Thr Val Asn Gly His Leu Asp Ser Tyr Glu Lys Val Thr
                195                 200                 205

Gln Leu Pro Gly Pro Ile Arg Glu Phe Leu Asp Gln Tyr Asp Ala Pro
210                 215                 220

Leu
225

<210> SEQ ID NO 25
<211> LENGTH: 212
<212> TYPE: PRT
<213> ORGANISM: Mus musculus

<400> SEQUENCE: 25

Met Val Ala Arg Asn Gln Val Ala Ala Asp Asn Ala Ile Ser Pro Ala
1               5                   10                  15

Ala Glu Pro Arg Arg Ser Glu Pro Ser Ser Ser Ser Ser Ser
                20                  25                  30

Ser Pro Ala Ala Pro Val Arg Pro Arg Pro Cys Pro Ala Val Pro Ala
                35                  40                  45

Pro Ala Pro Gly Asp Thr His Phe Arg Thr Phe Arg Ser His Ser Asp
        50                  55                  60

Tyr Arg Arg Ile Thr Arg Thr Ser Ala Leu Leu Asp Ala Cys Gly Phe
65                  70                  75                  80

Tyr Trp Gly Pro Leu Ser Val His Gly Ala His Glu Arg Leu Arg Ala
                85                  90                  95

Glu Pro Val Gly Thr Phe Leu Val Arg Asp Ser Arg Gln Arg Asn Cys
                100                 105                 110

Phe Phe Ala Leu Ser Val Lys Met Ala Ser Gly Pro Thr Ser Ile Arg
        115                 120                 125

Val His Phe Gln Ala Gly Arg Phe His Leu Asp Gly Ser Arg Glu Thr
        130                 135                 140

Phe Asp Cys Leu Phe Glu Leu Leu Glu His Tyr Val Ala Ala Pro Arg
145                 150                 155                 160

Arg Met Leu Gly Ala Pro Leu Arg Gln Arg Arg Val Arg Pro Leu Gln
                165                 170                 175

Glu Leu Cys Arg Gln Arg Ile Val Ala Val Gly Arg Glu Asn Leu
                180                 185                 190

Ala Arg Ile Pro Leu Asn Pro Val Leu Arg Asp Tyr Leu Ser Ser Phe
                195                 200                 205

Pro Phe Gln Ile
        210

<210> SEQ ID NO 26
<211> LENGTH: 1193
<212> TYPE: DNA
<213> ORGANISM: Mus musculus
```

<400> SEQUENCE: 26

```
ggcacggctc ccagcccegg agcatgcgcg acagccgccc cggagccccc agccgcggct      60
ccccgcgtcc tgccgccagc gcagccccgg acgctatggc ccaccectcc agctggcccc     120
tcgagtagga tggtagcacg caaccaggtg gcagccgaca atgcgatctc cccggcagca     180
gagccccgac ggcggtcaga gccctcctcg tcctcgtctt cgtcctcgcc agcggccccc     240
gtgcgtcccc ggccctgccc ggcggtccca gccccagccc ctggcgacac tcacttccgc     300
accttccgct cccactccga ttaccggcgc atcacgcgga ccagcgcgct cctggacgcc     360
tgcggcttct attggggacc cctgagcgtg cacggggcgc acgagcggct gcgtgccgag     420
cccgtgggca ccttcttggt gcgcgacagt cgccaacgga actgcttctt cgcgctcagc     480
gtgaagatgg cttcgggccc cacgagcatc cgcgtgcact ccaggccgg ccgcttccac      540
ttggacggca gccgcgagac cttcgactgc cttttcgagc tgctggagca ctacgtggcg     600
gcgccgcgcc gcatgttggg ggccccgctg cgccagcgcc gcgtgcggcc gctgcaggag     660
ctgtgtcgcc agcgcatcgt ggccgccgtg ggtcgcgaga acctggcgcg catccctctt     720
aacccggtac tccgtgacta cctgagttcc ttcccctccc agatctgacc ggctgccgct     780
gtgccgcagc attaagtggg ggcgccttat tatttcttat tattaattat tattattttt     840
ctggaaccac gtgggagccc tccccgcctg ggtcggaggg agtggttgtg gagggtgaga     900
tgcctcccac ttctggctgg agacctcatc ccacctctca ggggtggggg tgctcccctc     960
ctggtgctcc ctccgggtcc ccctggttg tagcagcttg tgtctgggc caggacctga     1020
attccactcc tacctctcca tgtttacata ttcccagtat ctttgcacaa accaggggtc    1080
ggggagggtc tctggcttca ttttttctgct gtgcagaata tcctatttta tattttttaca  1140
gccagtttag gtaataaact ttattatgaa agtttttttt taaaagaaac aaa           1193
```

<210> SEQ ID NO 27
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Met Gly Ser Ser His His His His His His Ser Ser Gly Leu Val Pro
1               5                   10                  15

Arg Gly Ser Met Val Ala Arg Asn Gln Val Ala Ala Asp Asn Ala Ile
            20                  25                  30

Ser Pro Ala Ala Glu Pro Arg Arg Ser Glu Pro Ser Ser Ser Ser
        35                  40                  45

Ser Ser Ser Ser Pro Ala Ala Pro Val Arg Pro Arg Pro Cys Pro Ala
    50                  55                  60

Val Pro Ala Pro Ala Pro Gly Asp Thr His Phe Arg Thr Phe Arg Ser
65                  70                  75                  80

His Ser Asp Tyr Arg Arg Ile Thr Arg Thr Ser Ala Leu Leu Asp Ala
                85                  90                  95

Cys Gly Phe Tyr Trp Gly Pro Leu Ser Val His Gly Ala His Glu Arg
            100                 105                 110

Leu Arg Ala Glu Pro Val Gly Thr Phe Leu Val Arg Asp Ser Arg Gln
        115                 120                 125

Arg Asn Cys Phe Phe Ala Leu Ser Val Lys Met Ala Ser Gly Pro Thr
    130                 135                 140
```

Ser Ile Arg Val His Phe Gln Ala Gly Arg Phe His Leu Asp Gly Ser
145                 150                 155                 160

Arg Glu Thr Phe Asp Cys Leu Phe Glu Leu Leu Glu His Tyr Val Ala
                165                 170                 175

Ala Pro Arg Arg Met Leu Gly Ala Pro Leu Arg Gln Arg Arg Val Arg
            180                 185                 190

Pro Leu Gln Glu Leu Cys Arg Gln Arg Ile Val Ala Ala Val Gly Arg
        195                 200                 205

Glu Asn Leu Ala Arg Ile Pro Leu Asn Pro Val Leu Arg Asp Tyr Leu
    210                 215                 220

Ser Ser Phe Pro Phe Gln Ile
225                 230

<210> SEQ ID NO 28
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Gly Ser Ser His His His His His His Ser Ser Gly Leu Val Pro
1               5                   10                  15

Arg Gly Ser Met Val Ala Arg Asn Gln Val Ala Ala Asp Asn Ala Ile
            20                  25                  30

Ser Pro Ala Ala Glu Pro Arg Arg Arg Ser Glu Pro Ser Ser Ser Ser
        35                  40                  45

Ser Ser Ser Ser Pro Ala Ala Pro Val Arg Pro Arg Pro Cys Pro Ala
50                  55                  60

Val Pro Ala Pro Ala Pro Gly Asp Thr His Phe Arg Thr Phe Arg Ser
65                  70                  75                  80

His Ser Asp Tyr Arg Arg Ile Thr Arg Thr Ser Ala Leu Leu Asp Ala
                85                  90                  95

Cys Gly Phe Tyr Trp Gly Pro Leu Ser Val His Gly Ala His Glu Arg
            100                 105                 110

Leu Arg Ala Glu Pro Val Gly Thr Phe Leu Val Arg Asp Ser Arg Gln
        115                 120                 125

Arg Asn Cys Phe Phe Ala Leu Ser Val Lys Met Ala Ser Gly Pro Thr
130                 135                 140

Ser Ile Arg Val His Phe Gln Ala Gly Arg Phe His Leu Asp Gly Ser
145                 150                 155                 160

Arg Glu Thr Phe Asp Cys Leu Phe Glu Leu Leu Glu His Tyr Val Ala
                165                 170                 175

Ala Pro Arg Arg Met Leu Gly Ala Pro Leu Arg Gln Arg Arg Val Arg
            180                 185                 190

Pro Leu Gln Glu Leu Cys Arg Gln Arg Ile Val Ala Ala Val Gly Arg
        195                 200                 205

Glu Asn Leu Ala Arg Ile Pro Leu Asn Pro Val Leu Arg Asp Tyr Leu
    210                 215                 220

Ser Ser Phe Pro Phe Gln Ile Ala Ala Val Leu Leu Pro Val Leu Leu
225                 230                 235                 240

Ala Ala Pro

<210> SEQ ID NO 29
<211> LENGTH: 243
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 29

Met Gly Ser Ser His His His His His His Ser Ser Gly Leu Val Pro
1               5                   10                  15

Arg Gly Ser Ala Ala Val Leu Leu Pro Val Leu Leu Ala Ala Pro Met
            20                  25                  30

Val Ala Arg Asn Gln Val Ala Ala Asp Asn Ala Ile Ser Pro Ala Ala
        35                  40                  45

Glu Pro Arg Arg Arg Ser Glu Pro Ser Ser Ser Ser Ser Ser Ser Ser
    50                  55                  60

Pro Ala Ala Pro Val Arg Pro Arg Pro Cys Pro Ala Val Pro Ala Pro
65                  70                  75                  80

Ala Pro Gly Asp Thr His Phe Arg Thr Phe Arg Ser His Ser Asp Tyr
                85                  90                  95

Arg Arg Ile Thr Arg Thr Ser Ala Leu Leu Asp Ala Cys Gly Phe Tyr
            100                 105                 110

Trp Gly Pro Leu Ser Val His Gly Ala His Glu Arg Leu Arg Ala Glu
            115                 120                 125

Pro Val Gly Thr Phe Leu Val Arg Asp Ser Arg Gln Arg Asn Cys Phe
    130                 135                 140

Phe Ala Leu Ser Val Lys Met Ala Ser Gly Pro Thr Ser Ile Arg Val
145                 150                 155                 160

His Phe Gln Ala Gly Arg Phe His Leu Asp Gly Ser Arg Glu Thr Phe
                165                 170                 175

Asp Cys Leu Phe Glu Leu Leu Glu His Tyr Val Ala Ala Pro Arg Arg
            180                 185                 190

Met Leu Gly Ala Pro Leu Arg Gln Arg Arg Val Arg Pro Leu Gln Glu
            195                 200                 205

Leu Cys Arg Gln Arg Ile Val Ala Ala Val Gly Arg Glu Asn Leu Ala
    210                 215                 220

Arg Ile Pro Leu Asn Pro Val Leu Arg Asp Tyr Leu Ser Ser Phe Pro
225                 230                 235                 240

Phe Gln Ile

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 30

His His His His His His
1               5
```